US011559310B2

(12) United States Patent
H'Doubler

(10) Patent No.: US 11,559,310 B2
(45) Date of Patent: Jan. 24, 2023

(54) AORTIC OCCLUSION BALLOON APPARATUS, SYSTEM AND METHOD OF MAKING

(71) Applicant: William H'Doubler, Roanoke, VA (US)

(72) Inventor: William H'Doubler, Roanoke, VA (US)

(73) Assignee: William H'Doubler, Roanoke, VA (US)

( * ) Notice: Subject to any disclaimer, the term of this patent is extended or adjusted under 35 U.S.C. 154(b) by 204 days.

(21) Appl. No.: 16/547,821

(22) Filed: Aug. 22, 2019

(65) Prior Publication Data

US 2019/0374231 A1  Dec. 12, 2019

Related U.S. Application Data

(63) Continuation of application No. 15/588,698, filed on May 8, 2017, now Pat. No. 10,433,852.

(51) Int. Cl.
*A61B 17/12* (2006.01)
*A61M 5/00* (2006.01)
(Continued)

(52) U.S. Cl.
CPC .... *A61B 17/12136* (2013.01); *A61B 17/1204* (2013.01); *A61M 5/007* (2013.01); *A61M 25/005* (2013.01); *A61M 25/0662* (2013.01); *A61M 25/10182* (2013.11); *A61B 17/12109* (2013.01); *A61M 25/007* (2013.01); *A61M 25/0052* (2013.01); *A61M 2005/006* (2013.01); *A61M 2025/0076* (2013.01);
(Continued)

(58) Field of Classification Search
CPC ....... A61B 17/12136; A61B 17/12109; A61M 25/10182; A61M 5/007; A61M 25/005; A61M 25/007; A61M 2005/006; A61M 2025/0076; A61M 2025/105; A61M 2202/0478
See application file for complete search history.

(56) References Cited

U.S. PATENT DOCUMENTS 3,833,003 A   9/1974  Taricco
4,404,971 A   9/1983  Leveen
(Continued)

OTHER PUBLICATIONS

Nonfinal Office Action in Parent Case U.S. Appl. No. 15/588,698, dated May 18, 2018.
(Continued)

*Primary Examiner* — Manuel A Mendez
(74) *Attorney, Agent, or Firm* — Reston Law Group, LLP; Ralph P. Albrecht

(57) ABSTRACT

The disclosure sets forth various exemplary embodiments of systems, methods, and/or medical apparatuses including but not limited to: a sheath; and a balloon disposed at a working distal end of the sheath. According to one example embodiment the medical device can include where the sheath can include woven wire reinforcing axial and longitudinal strength, side holes, a one direction distal valve, and can include an inflator. According to one example embodiment the medical device can include where the sheath can include a narrow cross-section of, e.g., 7-8 Fr and balloon of length of, e.g., 12 cm.

24 Claims, 9 Drawing Sheets

(51) Int. Cl.
*A61M 25/10* (2013.01)
*A61M 25/00* (2006.01)
*A61M 25/06* (2006.01)

(52) U.S. Cl.
CPC .......... *A61M 2025/105* (2013.01); *A61M 2025/1052* (2013.01); *A61M 2202/0225* (2013.01); *A61M 2202/0478* (2013.01)

(56) References Cited

U.S. PATENT DOCUMENTS

| | | | |
|---|---|---|---|
| 4,444,186 A | | 4/1984 | Wolvek |
| 4,445,892 A | | 5/1984 | Hussein et al. |
| 4,540,404 A | | 9/1985 | Wolvek |
| 4,569,347 A | * | 2/1986 | Frisbie .................. A61M 29/02 604/164.05 |
| 4,752,286 A | * | 6/1988 | Okada .................... A61B 17/12 604/104 |
| 4,773,899 A | | 9/1988 | Spears |
| 4,777,951 A | * | 10/1988 | Cribier .............. A61M 25/0023 600/485 |
| 4,917,667 A | * | 4/1990 | Jackson ............ A61M 25/0075 604/103 |
| 5,030,227 A | | 7/1991 | Rosenbluth et al. |
| 5,090,959 A | | 2/1992 | Samson et al. |
| 5,100,429 A | | 3/1992 | Sinofsky et al. |
| 5,318,529 A | | 6/1994 | Kontos |
| 5,344,419 A | | 9/1994 | Spears |
| 5,411,016 A | | 5/1995 | Kume et al. |
| 5,454,788 A | | 10/1995 | Walker |
| 5,490,859 A | | 2/1996 | Mische et al. |
| 5,632,762 A | | 5/1997 | Myler |
| 5,693,015 A | | 12/1997 | Walker |
| 5,728,065 A | * | 3/1998 | Follmer ................ A61M 25/10 604/96.01 |
| 5,728,066 A | * | 3/1998 | Daneshvar ........... A61M 25/10 604/113 |
| 5,759,174 A | | 6/1998 | Fischell et al. |
| 6,186,978 B1 | * | 2/2001 | Samson ............. A61M 25/005 604/525 |
| 6,231,544 B1 | | 5/2001 | Tsugita |
| 6,322,534 B1 | * | 11/2001 | Shkolnik ............ A61M 25/005 604/96.01 |
| 6,527,791 B2 | | 3/2003 | Fisher |
| 6,589,264 B1 | | 7/2003 | Barbut |
| 6,689,152 B2 | | 2/2004 | Balceta |
| 7,160,318 B2 | | 1/2007 | Greenberg |
| 7,169,140 B1 | | 1/2007 | Kume |
| 7,862,609 B2 | | 1/2011 | Butaric et al. |
| 8,147,534 B2 | | 4/2012 | Berez |
| 8,163,004 B2 | | 4/2012 | Amplatz |
| 8,257,381 B2 | | 9/2012 | Dillard |
| 8,273,101 B2 | | 9/2012 | Garcia |
| 8,491,648 B2 | | 7/2013 | Hassan |
| 8,651,007 B2 | | 2/2014 | Adams |
| 8,679,171 B2 | | 3/2014 | Deem |
| 8,747,453 B2 | | 6/2014 | Amplatz et al. |
| 8,813,625 B1 | | 8/2014 | Janardhan |
| 8,828,045 B1 | | 9/2014 | Janardhan |
| 8,845,675 B2 | | 9/2014 | Johnson |
| 8,900,287 B2 | | 12/2014 | Amplatz |
| 9,149,381 B2 | | 10/2015 | Schreck |
| 9,198,666 B2 | | 12/2015 | Berez |
| 9,248,262 B2 | | 2/2016 | Mukherjee |
| 9,295,569 B2 | | 3/2016 | Kim |
| 9,381,104 B2 | | 7/2016 | Berez |
| 9,408,609 B2 | | 8/2016 | Kassab |
| 9,408,688 B2 | | 8/2016 | Deem |
| 9,474,507 B2 | | 10/2016 | Havel |
| 9,474,882 B2 | | 10/2016 | Franklin |
| 9,532,785 B2 | | 1/2017 | Hassan |
| 9,555,166 B2 | | 1/2017 | Kutryk |
| 9,561,096 B2 | | 2/2017 | Kim |
| 9,561,097 B1 | | 2/2017 | Kim et al. |
| 9,561,122 B2 | | 2/2017 | Kusleika |
| 9,629,636 B2 | | 4/2017 | Fogarty |
| 9,687,366 B2 | | 6/2017 | Golden |
| 9,687,374 B2 | | 6/2017 | Schreck |
| 9,700,402 B2 | | 7/2017 | Kassab |
| 2007/0168018 A1 | | 7/2007 | Amplatz et al. |
| 2009/0287145 A1 | | 11/2009 | Cragg et al. |
| 2010/0063578 A1 | | 3/2010 | Ren et al. |
| 2010/0280451 A1 | | 11/2010 | Teeslink et al. |
| 2011/0137245 A1 | | 6/2011 | Schaeffer et al. |
| 2012/0016297 A1 | * | 1/2012 | D'Aquanni ........... A61L 29/126 604/96.01 |
| 2013/0073024 A1 | | 3/2013 | Russo et al. |
| 2013/0102926 A1 | | 4/2013 | Eliason et al. |
| 2014/0243873 A1 | | 8/2014 | Franklin |
| 2015/0327836 A1 | | 11/2015 | Stone |
| 2016/0206798 A1 | | 7/2016 | Williams et al. |
| 2017/0128240 A1 | | 5/2017 | Deem |

OTHER PUBLICATIONS

Final Office Action in Parent Case U.S. Appl. No. 15/588,698, dated Dec. 21, 2018.

* cited by examiner

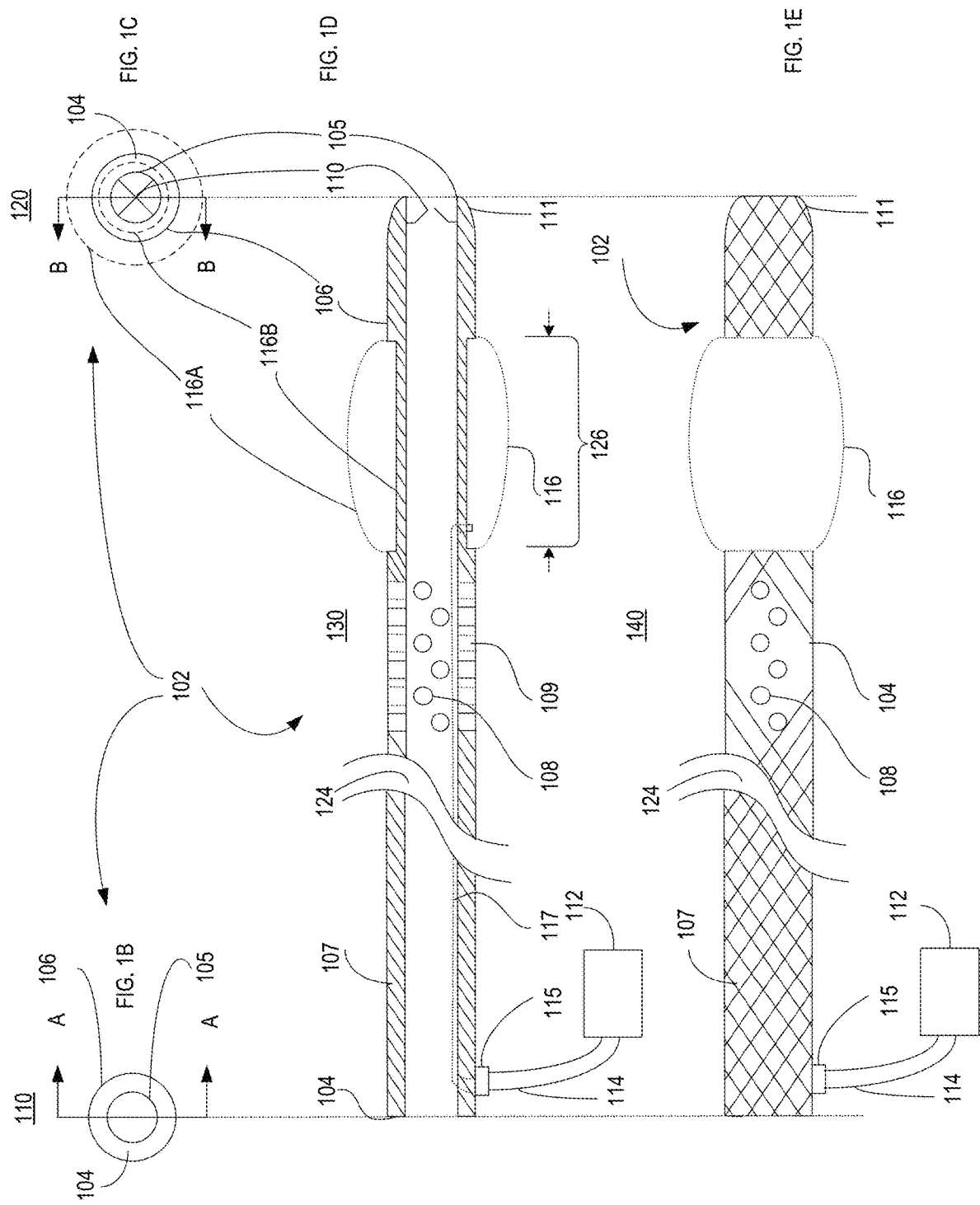

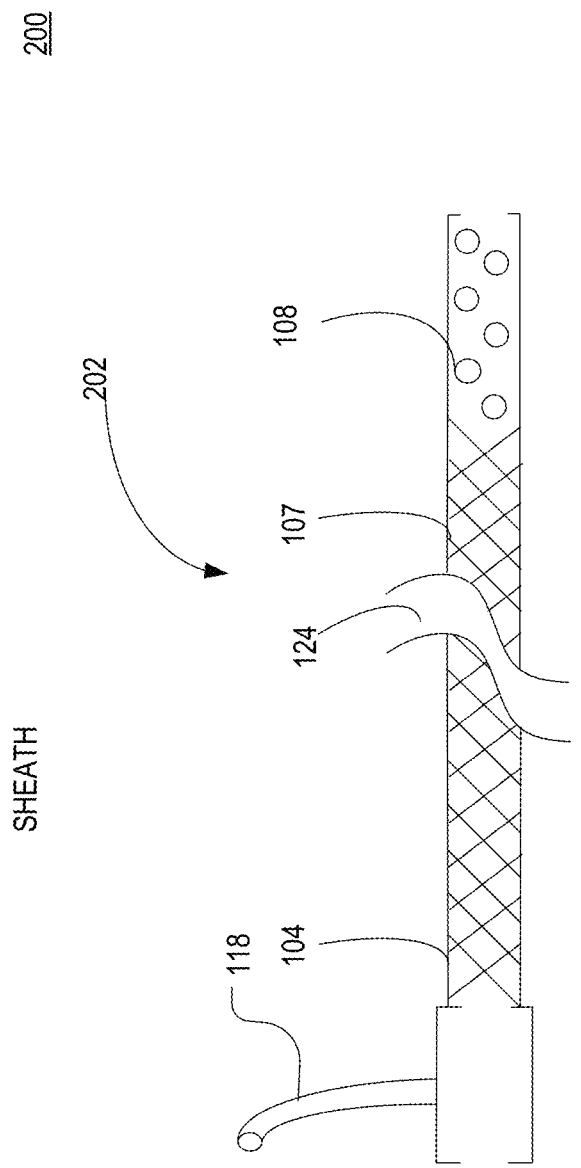

AORTIC OCCLUSION BALLOON APPARATUS, SYSTEM AND METHOD OF MAKING

CROSS-REFERENCE TO RELATED PATENT APPLICATIONS

This application is a continuation of, and claims priority under 35 USC Section 120 of, U.S. patent application Ser. No. 15/588,698, filed May 8, 2017, the contents of all of which, is incorporated herein by reference in its entirety.

BACKGROUND OF THE DISCLOSURE

Technical Field of the Disclosure

The disclosure relates generally to treatment of aneurysms and trauma, and therapies seeking to reinforce, or occlude, a blood vessel. Although emphasis is given to repair of ruptured aneurysms and particularly iliac artery and abdominal aortic aneurysm (AAA), other embodiments are suitable for applications in treating trauma patients.

Related Art

An abdominal aortic aneurysm (AAA) is a weak area in the aorta, a sac in an arterial wall caused by an abnormal dilation of the wall of the aorta, a major artery of the body, as it passes through the abdomen of a patient's body from heart toward the legs. The abdomen is a portion of the body which lies between the thorax and the pelvis. The abdomen contains a cavity, known as the abdominal cavity, separated by the diaphragm from the thoracic cavity and is lined with a serous membrane, the peritoneum. The aorta is the main trunk, or artery, from which the systemic arterial system proceeds. The aorta arises from the left ventricle of the heart, passes upward, bends over and passes down through the thorax, through the abdomen to about the level of the fourth lumbar vertebra, where it divides into the two common iliac arteries. The normal diameter of the abdominal aorta is about one inch (25 mm), but blood vessels of smaller people, and the elderly can be smaller. As blood flows through the aorta, the weakened area can bulge like a balloon and can burst (referred to as rupturing) if the balloon gets too enlarged.

Most aortic aneurysms occur in the abdominal aorta, caused primarily by arteriosclerosis. This is a condition in which fatty deposits are laid down in the walls of arteries, causing the blood vessel to become weakened and less elastic. Risk factors for arteriosclerosis include high blood pressure, smoking, and genetic factors. The AAA usually arises in the infrarenal portion of the arteriosclerotically diseased aorta such as, for example, below the kidneys. When left untreated, an AAA can eventually cause rupture of the sac with ensuing fatal hemorrhaging in a very short time. High mortality associated with rupture of an AAA has led to the development of methods of transabdominal surgical repair of abdominal aortic aneurysms. Surgery involving the abdominal wall, however, is a major undertaking with associated high risks. There is considerable risk associated with this surgical intervention, which can involve replacing a diseased and aneurysmal segment of blood vessel with a prosthetic device which can typically be a synthetic tube, stent, or graft, usually fabricated of either DACRON®, GORETEX®, or other suitable material. Examples of stent graft systems include the ENDURANT® II, stent grafts systems available from Medtronic Corporation of Minneapolis, Minn. USA and/or a GORE® EXCLUDER® AAA Endoprosthesis, available from Gore Medical, a division of W.L. Gore & Associates, Inc., Medical Products Division, Flagstaff, Ariz., USA.

A first conventional method of performing the surgical procedure, can include exposure of the aorta through an abdominal incision, which could extend from the rib cage to the pubis. The aorta must be closed both above and below the aneurysm, so that the aneurysm can then be opened and the thrombus, or blood clot, and arteriosclerotic debris removed. Small arterial branches from the back wall of the aorta can be tied off. The DACRON® or GORETEX® tube, or graft, of approximately the same size of the normal aorta can be sutured in place, thereby replacing the aneurysm. Blood flow can then be reestablished through the graft. With this method, it can be necessary to move the intestines in order to get to the back wall of the abdomen prior to clamping off the aorta.

If the surgery is performed prior to rupture of the abdominal aorta aneurysm, the survival rate of treated patients is markedly higher than if the surgery is performed after the aneurysm ruptures, although the mortality rate is still quite high. If surgery is performed prior to rupture of the aneurysm, the mortality rate is minimal. Conventional surgery performed after rupture of the aneurysm results in a significantly higher mortality rate. Although abdominal aortic aneurysms can be detected from routine examinations, patients do not experience any pain from the condition. Thus, if the patient is not receiving routine examinations, it is possible that an aneurysm can progress to the rupture stage undetected.

Disadvantages associated with the first conventional surgery, in addition to high mortality rate, include an extended recovery period associated with such surgery; difficulties in suturing the graft, or tube, to the aorta; loss of the existing thrombosis to support and reinforce the graft; unsuitability of the surgery for many patients having abdominal aortic aneurysms; and problems associated with performing the surgery on an emergency basis after the aneurysm has ruptured. As to the extent of recovery, a patient can expect to spend 1 to 2 weeks in the hospital after surgery, a major portion of which is spent in the intensive care unit, and a convalescence period at home follows, particularly if the patient has other illnesses such as heart, lung, liver, and/or kidney disease, in which case the hospital stay can also be lengthened. Since the graft must be secured, or sutured, to the remaining portion of the aorta, it can many times be difficult to perform the suturing step because of thrombosis present on the remaining portion of the aorta, and that remaining portion of the aortic wall may be weakened.

More recently, a second conventional approach to repair an abdominal aortic aneurysm can include intraluminal graft delivery. Vascular surgeons install an endovascular stent/graft delivered to the site of the aneurysm using elongated catheters threaded through a patient's blood vessels, often over a wire. Typically, the surgeon makes a small incision in the patient's groin area and inserts a delivery catheter containing a collapsed, self-expanding, or balloon expandable stent/graft to a location bridging the aneurysm, at which point the stent/graft can be delivered out from the distal end of the delivery catheter and can be allowed or made to expand to approximately the normal diameter of the aorta at that location. The stent/graft is a tubular structure allowing blood flow through the lumen thereof and removing pressure from the aneurysm. Over time the stent/graft can become endothelialized and space between the outer wall of the stent and the aneurysm can fill with clotted blood. After installation, the aneurysm is no longer subjected to aortic pressure and thus will no longer continue to grow. Intraluminal stent graft delivery does not have a relatively high mortality rate; does not have an extended recovery period; does not require suturing the graft to the remaining aorta wall; permits existing thrombosis to support and reinforce the graft; is suitable for older patients; and is more readily performed on an emergency basis after rupture of the aneurysm.

Unfortunately patients who suffer from a ruptured AAA can experience extensive internal bleeding, and an associated loss of blood pressure, that can lead to brain injury. Thus, what is needed is an improved method of occluding blood flow caused by a ruptured aneurysm or traumatic injury to prevent brain injury and to allow implantation of implantable stent graft in the ruptured portion of the aorta.

In a trauma setting, limiting or stopping blood flow through the major blood vessel of the body, the aorta, is an established method for slowing the rate of blood loss in a severely injured patient with ongoing bleeding. In the military, this aortic occlusion has traditionally been achieved using a large aortic clamp inserted into the chest cavity via a large incision between the ribs. This extremely invasive maneuver is often reserved only for the sickest patients who have lost vital signs. Clamping the aorta excludes the systemic circulation, by definition, thus causing an ischemia. The goal of aortic clamping is to keep the patient's remaining blood circulating to the heart, lungs, and brain until bleeding below the aortic clamp is controlled and the patient can be resuscitated and systemic circulation restored.

Recently, balloon catheters used in endovascular surgery have been repurposed to occlude the aorta by inflation of a balloon in the lumen of the aorta, as an alternative to aortic clamping. This procedure is referred to as resuscitative endovascular balloon occlusion of the aorta (REBOA). REBOA has potential to achieve effective aortic occlusion. Therefore, REBOA may be used in a bleeding patient.

As with aortic clamping, REBOA can be used to increase blood pressure to vital organs while slowing ongoing blood loss. However, currently available FDA-approved balloon catheters used for REBOA can become dislodged when blood pressure resumes due to bowing of the flexible stem of conventional balloon occlusion catheters. An example of this type of device is disclosed in Eliason et al., U.S. Patent Application Publication No. 2013/0102926, published Apr. 25, 2013, which is incorporated herein by reference in its entirety. As such, conventional balloon occlusion has shortcomings. When aortic occlusion is used in the course of treatment of a hemorrhaging trauma patient, the physician must also begin to wean the patient off occlusion as early as possible. Using REBOA, when the balloon is inflated, everything below the balloon quickly starts to die due to lack of blood flow. When the balloon is deflated to initiate flow, hemodynamic collapse is possible. Additionally, variation in patient size (height, weight, aortic diameter) limits the ability of a REBOA catheter to effectively occlude aortic flow in all patients.

What is needed is an improved solution that overcomes the shortcomings of conventional solutions.

SUMMARY

The disclosure sets forth various exemplary embodiments of systems, methods, and/or medical apparatuses including but not limited to: a sheath; and an elongate balloon occlude disposed at a working distal end of the sheath.

According to one example embodiment the medical device can include where the sheath can include but is not limited to: woven wire reinforcing axial or longitudinal strength. In one exemplary embodiment, the wire can be Nitinol, steel, or other commonly used medical wire.

According to one example embodiment the medical device can include where the sheath can include but is not limited to: a narrow cross-section.

According to one example embodiment the medical device can include where the narrow cross-section sheath can include but is not limited to an external cross-sectional diameter of at least one of: 5-10 Fr; 6-9 Fr; 6-7 Fr; or 8 Fr or less.

According to one example embodiment the medical device can include where the sheath can include but is not limited to: at least one hole.

According to one example embodiment the medical device can include where the at least one hole of the sheath can include but is not limited to at least one of: at least one side hole; a one-way valve; a one-way valve at a distal tip of the sheath; or a one-way valve on a distal end, distal to the balloon.

According to one example embodiment the medical device can include where the at least one hole of the sheath can include but is not limited to: a plurality of side holes; and a one-way valve on a distal end, distal to the balloon.

According to one example embodiment the medical device can include where the sheath further can include but is not limited to: a lumen can include but is not limited to at least one channel for use in dispensing via the at least one hole at least one of: a radio opaque dye; a radio opaque gas; a $CO_2$ gas; an anti-coagulant; a heparin injection; or a drug.

According to one example embodiment the medical device can include where wherein the sheath further can include but is not limited to: a lumen can include but is not limited to at least one internal channel for use in dispensing at least one of: a radio opaque dye; anti-coagulant; or a drug.

According to one example embodiment the medical device can include where the balloon can include but is not limited to: wherein the balloon is recessed in a cavity in the sheath.

According to one example embodiment the medical device can include where the balloon can include but is not limited to: wherein the balloon is integrated coaxially in a cavity in the sheath.

According to one example embodiment the medical device can include where the balloon can include but is not limited to: wherein the balloon is coupled to an inflator.

According to one example embodiment the medical device can include where the balloon and inflator are coupled together via at least one of: lumen; or inflation port.

According to one example embodiment the medical device can include where the inflator can include but is not limited to at least one of: a syringe; a compressed gas source; a fluid source; a $CO_2$ cartridge; a hypodermic syringe; a pressurized air; a pressurized gas; or a pressurized liquid.

According to one example embodiment the medical device can include where the balloon can include but is not limited to: wherein the balloon has an inflation diameter at least of one of: 10 mm-60 mm (30-150 Fr); 15 mm-48 mm (45-144 Fr); or 44 mm (132 Fr).

According to one example embodiment the medical device can include where the balloon can include but is not limited to: wherein the balloon has balloon has a longitudinal length of at least one of: 9-15 cm (270-450 Fr); or 12 cm (360 Fr).

According to one example embodiment the medical device can further include but is not limited to: a lumen coupled to the sheath wherein the lumen is configured to: flush the sheath; or inject gas or fluid through the sheath.

According to one example embodiment the medical device can further include but is not limited to at least one of: a wire for passing the medical device through the vasculature of a patient; an introducer; an atraumatically tipped introducer; a rounded end introducer; an introducer configured to introduce the medical device through the vasculature of a patient; an introducer configured to pass over a wire the medical device;

According to one example embodiment the medical device can include where the woven wire can include but is not limited to: wherein the woven wire forms a mesh circumferentially embedded or adjacent to a lumen of the sheath.

According to one example embodiment the medical device can include where the sheath can include but is not limited to at least one polymer material can include but is not limited to at least one of: PS, ABS, SAN, PMMA, PPE, PP, PE, PA, PC, PET, PA, POM, PMP, PPP, PC-HT, PEI, PSU, PES, PPSU, PAI, PI, PVDF, ETFE, PCTFE, PTFE, ePTFE, PFA, LCP, PPS, PEEK, PEK, PEKEKK, FEP, PFA, nylon, fluoropolymer, LCP, or engineered plastic.

BRIEF DESCRIPTION OF THE DRAWINGS

The accompanying drawings, which are included to provide a further understanding and are incorporated in and constitute a part of this specification, illustrate exemplary, and nonlimiting embodiments and together with the description serve to explain the principles disclosed herein. In the drawings, like reference numbers may indicate substantially similar, equivalent, or exemplary elements, and the left most digits in the corresponding reference number indicate the drawing in which an element first appears.

The subject matter disclosed herein is particularly pointed out and distinctly claimed as set forth in the claims at the conclusion of the specification. The foregoing and other objects, features and advantages will be apparent from the following detailed description taken in conjunction with the accompanying drawings, of which:

FIG. 1B depicts an exemplary embodiment of an exemplary left end orthogonal view drawing 110 of the exemplary balloon sheath medical device, according to an exemplary embodiment;

FIG. 1C depicts an exemplary embodiment of an exemplary right end orthogonal view drawing of the exemplary balloon sheath medical device, illustrating an exemplary tip valve opening, according to an exemplary embodiment;

FIG. 1D depicts an exemplary embodiment of an exemplary cross-sectional view of an exemplary balloon sheath medical device, having exemplary side holes, and illustrating an exemplary valve on a right distal tip, according to an exemplary embodiment;

FIG. 1E depicts an exemplary embodiment of an exemplary external side view of an exemplary balloon sheath medical device illustrating exemplary longitudinal, axial strengthening wire wrapping, exemplary side holes, exemplary inflated balloon stint, according to an exemplary embodiment;

FIG. 2 depicts an exemplary embodiment of an exemplary drawing of an exemplary sheath medical device with exemplary side holes, according to an exemplary embodiment;

DETAILED DESCRIPTION OF VARIOUS EXEMPLARY EMBODIMENTS

Figure 1A:
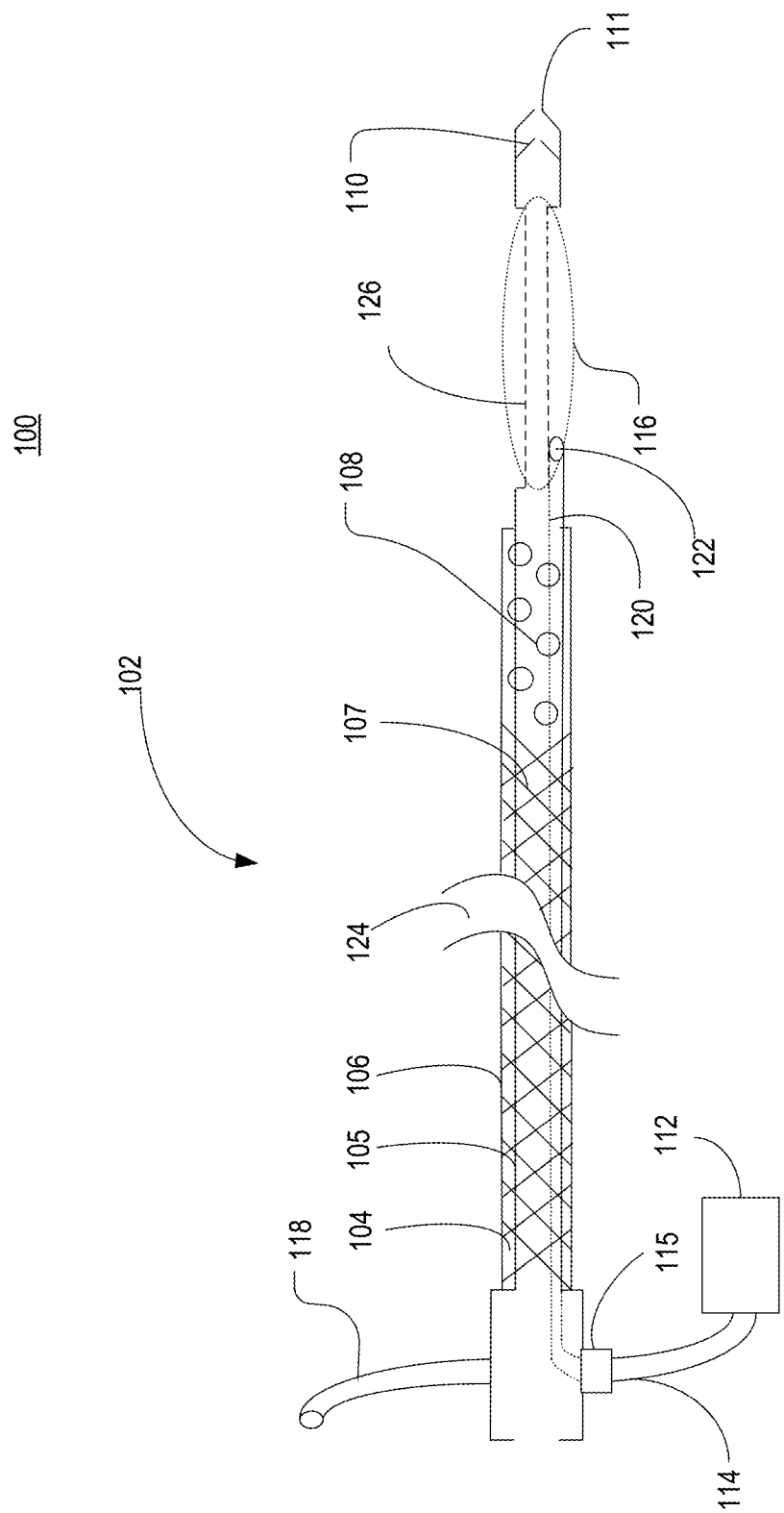
FIG. 1A depicts an exemplary embodiment of an exemplary drawing of an exemplary balloon sheath medical device, according to an exemplary embodiment.

It is important to note that the embodiments disclosed are only examples of the many advantageous uses of the innovative teachings herein. In general, statements made in the specification of the present application do not necessarily limit any of the various claims. Moreover, some statements may apply to some exemplary features but not to others. In general, unless otherwise indicated, singular elements may be in plural and vice versa with no loss of generality. In the drawings, like numerals refer to like parts through several views.

Overview

According to one exemplary embodiment, a rigid sheath can be provided along with an integrated, elongated balloon occlusion catheter, in one embodiment. In one exemplary embodiment, the elongated balloon occlusion catheter can be shaped like a hotdog when blown up, to provide additional external surface area to provide improved occlusion, as compared to conventional stent graft occlusion balloon catheters. In one exemplary embodiment, the rigid sheath can include a cross-sectional diameter of approximately in the range of, e.g., 7-9 Fr, significantly smaller in diameter than a conventional sheath. In an embodiment, the sheath may be reinforced with metal wire to increase longitudinal strength to avoid bowing when used in occluding blood flow in the thoracic region of the aorta, e.g., during treatment of trauma or AAA. In one exemplary embodiment, the improved occlusion balloon can include an elongated or oblong balloon of 10-14 cm, preferably about 12 cm length along a longitudinal axis. According to an exemplary embodiment, rapid inflation/deflation can be achieved by an inflator such as, e.g., but not limited to, or other gas, liquid, or fluid, hypodermic syringe, or the like. A compressed $CO_2$ cartridge, may be used as an inflator in one exemplary embodiment. According to an exemplary embodiment, the rigid sheath can include one or more holes, which can be along a side of, or at a distal working end, for example, for fluoroscopy, the use of infusing x-ray or radio opaque dye or gas, performing an angiogram, or infusing heparin or other anti-coagulants, etc. According to one exemplary embodiment, the rigid sheath can include a plurality of side holes. According to another exemplary embodiment, the rigid sheath can include a one directional valve, preferably at a distal end, for use in infusion of anticoagulants or other treatment, or may alternatively include a radio opaque tip. In one embodiment, the one-directional valve may be on a distal working tip of the rigid sheath, beyond the integrated balloon of an exemplary embodiment.

In an exemplary embodiment, the sheath can be constructed of resilient stiff plastic, nylon, polymer, or other stiff material, but can be of a small enough diameter, approximately 7-8 french to allow intraluminal endovascular deployment. In one embodiment, the medical device can be inserted, and later can be removed outside of an endovascular endograft stent, which may be implanted in the region of the common iliac. In one exemplary embodiment, the sheath can be integrated with or, wrapped in a wire mesh, such as, e.g., but not limited to, a Nitinol, shape memory metal, or other wire material mesh, in order to provide increased longitudinal strength as compared to conventional sheaths. According to one exemplary embodiment, rather than using a hypodermic syringe and air fluid for inflating/deflating the balloon, as is conventional, an exemplary $CO_2$ cartridge can be provided to allow improved capability such as, e.g., but not limited to, for faster inflation, radio opacity, etc., to blow up the elongated balloon occluder.

In one exemplary embodiment, behind and the proximal to the balloon, the sheath may include one or more holes in the side of the wall of the sheath, to allow for an Angiogram, or radio image, etc., or allowing infusion of heparin or other anti-coagulant, or other type of infusion, to be administered.

According to an exemplary embodiment, the distal end of the sheath may include a one-way valve, to allow unidirectional flow out through a distal tip of the sheath. The distal end may be rounded or otherwise atraumatic in shape, and the medical device, including the balloon occluder and the sheath may be configured to be introduced, over a wire, using, e.g., but not limited to, a plastic atraumatically tipped introducer, according to an exemplary embodiment.

Introduction

Intraluminal delivery of a graft stent up through the groin, can be delivered over a wire up through a femoral artery of the leg up into the common iliac region, and up into the lower abdominal portion of the aorta. In order to allow for implantation of an endograft stent in this region, it may be helpful to occlude blood flow coming down from the upper thoracic region of the aorta, to allow blood pressure to increase, during treatment of a ruptured abdominal aortic aneurysm (AAA), and to avoid brain injury due to lack of blood flow to the brain due to the ruptured AAA. According to an exemplary embodiment, a balloon occlusion catheter can be delivered up to the thoracic region, and can be blown up, e.g., with air or with liquid from a syringe through a tube coupled to the balloon. The use of the balloon occlusion catheter, as noted, can be used to prevent blood flow down the aorta, allowing resuscitation efforts, allowing graft stent implantation, and ensuring blood flow to the patient's brain. Unfortunately, conventional aortic occlusion balloons tend to migrate caudally (toward the tail end of the body) due to bowing of the flexible inflation lumen. According to an exemplary embodiment, an improved occlusion balloon can be supported by a rigid sheath, conventionally a large (14-16 French (Fr) sheath, where three (3) French is roughly equivalent to a one (1) millimeter) size sheath. Unfortunately, such a large sheath cannot be used in a small patient or a patient with small arteries. Conventionally, as the patient recovers, because of increasing pressure of the blood being pumped by the heart down through the aorta, the conventional flexible tubing attached to the balloon occlusion catheter can buckle or bow from the blood's pressure, causing the balloon to migrate and preventing the balloon from staying in a fixed position, and preventing proper occlusion. According to various exemplary embodiments, various improvements are set forth herein to overcome shortcomings of conventional small diameter balloon occluders with flexible inflation lumens. Various disclosed exemplary embodiments can overcome such shortcomings of conventional solutions, and may be used in treatment of ruptured AAA, as well as in a trauma setting to occlude blood flow in a trauma patient.

General Terminology

As will be apparent to those skilled in the art, the French scale or French gauge system is commonly used to measure the size of a catheter. The French scale is most often abbreviated as Fr (as it will be hereafter referred to, herein), but can often be seen abbreviated as Fg, Ga, FR or F. It may also be abbreviated as CH or Ch (for Charrière, its inventor). The French size is three times the diameter in millimeters. Thus, a round catheter of 1 French has an external diameter of ⅓ mm, and therefore the diameter of a round catheter in millimeters can be determined by dividing the French size by 3, see, e.g., Equations 1A and 1B:

$$D(\text{mm})=Fr/3 \qquad \text{Eq. 1A}$$

$$Fr=D(\text{mm})*3 \qquad \text{Eq. 1B}$$

For example, if the French size is 9, the diameter is 9/3=3.0 mm.

From the basic math equation for circumference (C)=πd, where d is the diameter of the circular cross-section, it follows that the catheter's circumference in mm is only slightly (about 4.7%) greater than the French size.

An increasing French size corresponds to a larger external diameter. This is contrary to needle-gauge size, where an increasing gauge corresponds to a smaller diameter needle.

The French size is a measure of the external diameter of a catheter (not internal drainage channel). So, for example, if a two-way catheter of 20 Fr is compared to a 20 Fr three-way catheter, they both have the same external diameter but the two-way catheter will have a larger drainage channel than the three-way. Three-way catheters accommodate an extra channel for irrigation within a similar external diameter.

The French gauge was devised by Joseph-Frederic-Benoit Charrire, a 19th-century Parisian maker of surgical instruments, who defined the "diameter times 3" relationship.

DETAILED DESCRIPTION

FIG. 1A depicts an exemplary embodiment of an exemplary drawing 100 of an exemplary balloon sheath medical device 102, according to an exemplary embodiment. Exemplary balloon sheath medical device 102 can include, in one example embodiment, an example plastic tube sheath 104 having an inner diameter 105, and an outer diameter 106. The balloon sheath medical device 102 can include the inner diameter wide enough to accept an exemplary introducer 602 with a steering guide wire 632 as depicted in exemplary FIG. 6, drawing 600, which can be used to guide and maneuver the exemplary balloon sheath medical device 102 to the upper thoracic region 810 (see FIG. 8) of the aorta, with a one-way valve 110 at a distal tip 111, to allow, e.g., but not limited to, for introduction of a radio opaque (not permitting the passage of x-rays or other radiant energy) contrast medium that can be injected into the body, according to an exemplary embodiment. The radio opaque contrast medium may be introduced via catheter, to the upper thoracic region of the aorta, to facilitate radiographic imaging of internal structures that otherwise are difficult to visualize on x-ray displays, contrast media may be either radiopaque or radiolucent, according to an exemplary embodiment. The balloon sheath medical device 102 catheter can include an exemplary wire wrap or support 107, in an exemplary embodiment, providing longitudinal axial strength, according to an exemplary embodiment. The balloon sheath medical device 102 catheter can include an exemplary one or more holes 108, which may be on the side of the plastic tube sheath 104, or may be on an end or distal working end tip 111, according to an exemplary embodiment. As shown, exemplary sheath 104 may include an exemplary optional flush tube 118, according to one exemplary embodiment.

Figure 8:
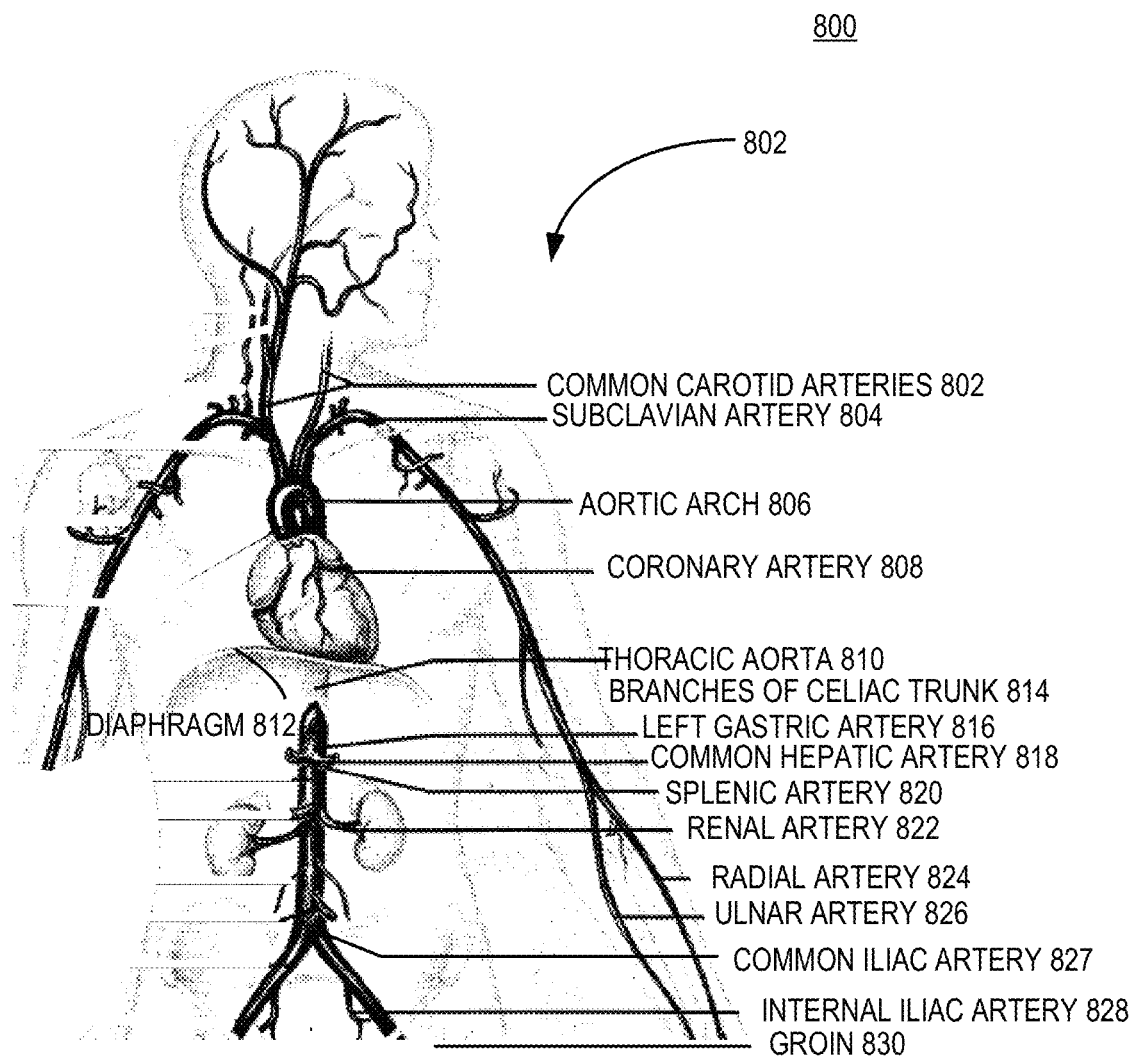
FIG. 8 depicts an exemplary embodiment of exemplary drawing, illustrating an exemplary representation of a patient's peripheral arterial system, according to an exemplary embodiment.

Example plastic tube sheath 104, according to an exemplary embodiment, can be manufactured from any of various other polymer materials, as will be apparent to those skilled in the relevant art, including, e.g., but not limited to, PS, ABS, SAN, PMMA, PPE, PP, PE, PA, PC, PET, PA, POM, PMP, PPP, PC-HT, PEI, PSU, PES, PPSU, PAI, PI, PVDF, ETFE, PCTFE, PTFE, ePTFE, PFA, LCP, PPS, PEEK, PEK, PEKEKK, FEP, PFA, nylons, fluoropolymers, LCP, engineered plastics, and/or etc. Example materials, according to an exemplary embodiment, which may be used to manufacture various embodiments disclosed herein may include, e.g., but are not limited to, medical device materials available from any of various medical device vendors including Ensinger GmbH, Wilfried-Ensinger Strasse 1, 93413 Cham, Germany. As illustrated by cut away 124, the balloon sheath medical device 102 can be substantial length to permit reaching up from a groin region 830, up to thoracic aorta region 810 as illustrated in FIG. 8.

Balloon sheath medical device 102, according to an exemplary embodiment, can further include, an exemplary inflator 112, which according to one exemplary embodiment, can include one or more of a syringe, a hypodermic syringe, a pressurized cartridge, a pressurized gas cartridge, a compressor, a liquid and/or gas compressor, pneumatic and/or fluid, and/or $CO_2$ cartridge, etc. Thus, inflator 112 can include, in one embodiment a $CO_2$ cartridge, which can allow inflation of recessed balloon 116. Use of a $CO_2$ canister, according to an exemplary embodiment, for inflation can ease rapid inflation of the balloon occluder thus speeding up the procedure, as compared to conventional techniques.

According to an exemplary therapeutic endovascular use, the balloon sheath catheter medical device 102 can be used to inflate, via the inflator 112, the recessed balloon 116, according to an exemplary embodiment, to allow sheath medical device 102 to remain in a constant position to occlude blood flow, when the device is deployed in the upper thoracic region 810 of the aorta (see FIG. 8), to ensure blood flow to the brain of a patient, during, e.g., implantation in the region of the common iliac 827 of an abdominal stent graft such as, e.g., but not limited to, a GORE® EXCLUDER® AAA Endoprosthesis, available from Gore Medical, a division of W.L. Gore & Associates, Inc., Medical Products Division, Flagstaff, Ariz., USA, or an ENDURANT® II, or an ENDURANT Stent graft available from Medtronic Corporation.

Exemplary balloon sheath medical device 102 can further include, according to an exemplary embodiment, an example valve 110 on a distal end of the device, which can be a one way valve for infusion distal to the balloon. According to an exemplary embodiment, the balloon 116 can when inflated allow sheath medical device 102 to remain in a constant position to occlude blood flow, when the device is deployed in the upper thoracic region 810 of the aorta, to ensure blood flow to the brain of a patient, during, e.g., implantation of an abdominal stent graft, according to an exemplary embodiment.

Exemplary balloon sheath medical device 102 can further include, coupled to the exemplary inflator 112, various couplers, which can include being coupled via one or more tubes, lumen, and/or multi-lumen tubing, valves, and/or ports, and/or couplers, 114, 115, 120, 122 to an exemplary recessed balloon 116, according to an exemplary embodiment.

In one exemplary embodiment, the inflation couples 114, 115, 120, 122 can run internal, integrated with, and/or external to plastic tube sheath 104. Exemplary plastic tube sheath 114 can be integrated into, internal to, external to, or adjacent to a side of plastic tube sheath 104, and can be used to inflate, using example inflator 112, example recessed balloon 116, which as depicted can be placed in a recess of tubular sheath 104, according to an exemplary embodiment.

An exemplary recessed balloon 116, can in one embodiment be oblong in shape, oval, lengthened along one axis, tubular, or hotdog like in external volume, and/or can allow for delivery over a wire, similar to a conventional spherical balloon occlude catheter (see FIG. 7) such as, e.g., but not limited to, the RELIANT balloon catheter, available from MEDTRONIC, of 710 Medtronic Parkway, Minneapolis, Minn. 55432 USA. The balloon material can be of any exemplary medical grade material, such as, e.g., but not limited to, vinyl, nitrile, latex, silicone rubber, synthetic rubber, natural rubber, and/or vinyl latex, etc., according to an exemplary embodiment.

FIG. 1B depicts an exemplary embodiment of an exemplary left end orthogonal view drawing 110 of the exemplary balloon sheath medical device 102, according to an exemplary embodiment. Exemplary balloon sheath medical device 102 can include, in one example embodiment, an example plastic tube sheath 104 having an inner diameter 105, and an outer diameter 106, with inner diameter wide enough to accept an exemplary introducer 602 with a steering guide wire 632 (as depicted in exemplary FIG. 6, drawing 600), which can be used to guide and maneuver the exemplary balloon sheath medical device 102 to the upper thoracic region of the aorta, according to an exemplary embodiment.

FIG. 1C depicts an exemplary embodiment of an exemplary right end orthogonal view drawing 120 of the exemplary balloon sheath medical device 102, illustrating an exemplary valve opening 110 at working distal end tip 111, exemplary atraumatic blunt tip 111 with an orifice to accept steering guide wire 632, according to an exemplary embodiment. According to an exemplary therapeutic endovascular use, the balloon sheath catheter medical device 102 can be used to inflate, via the exemplary inflator 112, the exemplary recessed integrated balloon 116, with an inflated outer diameter 116A, having a recessed area or cavity in the sheath 104 that can house occlusion balloon 111, which can be blown up with the inflator 112 using, e.g., $CO_2$ so it could be inflated and deflated rapidly, inner diameter 116B, to get to the balloon to be smaller, and length 126, longer in longitudinal axis than conventional spherical balloon occluders to allow exemplary balloon sheath medical device 102 to remain in a constant position to occlude blood flow, according to an exemplary embodiment. Exemplary balloon sheath medical device 102 can include, in one example embodiment, an example plastic tube sheath 104 having an inner diameter 105, and an outer diameter 106, with inner diameter wide enough to accept an exemplary introducer 602 with a steering guide wire 632 as depicted in exemplary FIG. 6, drawing 600, which is used to guide and maneuver the exemplary balloon sheath medical device 102 to the upper thoracic region of the aorta, with an optical one-way valve 110 at the distal end to allow for, e.g., introduction of radio-opaque (not permitting the passage of x-rays or other radiant energy) contrast medium that can be injected into the body, introduced via catheter, to the upper thoracic region 810 of the aorta, to facilitate radiographic imaging of internal structures that otherwise are difficult to visualize on x-ray displays, contrast media may be either radiopaque or radiolucent, according to an exemplary embodiment.

FIG. 1D (similar to FIG. 1A drawing 102, but an alternative embodiment) depicts an exemplary embodiment of an exemplary cross-sectional view 130 of an exemplary balloon sheath medical device 102, having exemplary side holes 108, exemplary atraumatic blunt, or rounded distal working end tip 111 with one or more orifice(s) for steering guide wire 632, and illustrating an exemplary valve on a right distal tip, according to an exemplary embodiment. Exemplary balloon sheath medical device 102 can include, in one example embodiment, an example plastic tube sheath 104 having an inner diameter 105, and an outer diameter 106, with inner diameter 105 wide enough to accept an exemplary introducer 602 with a steering guide wire 632 as depicted in exemplary FIG. 6, drawing 600, which can be used to guide and maneuver the exemplary balloon sheath medical device 102 to the upper thoracic region 810 of the aorta. According to an exemplary embodiment, the device 102 can include an exemplary one-way valve 110 at the tip 111 to allow for introduction of e.g., but not limited to, radio-opaque (not permitting the passage of x-rays or other radiant energy) contrast medium that is injected into the body, introduced via catheter, to the upper thoracic region of the aorta, to facilitate radiographic imaging of internal structures that otherwise are difficult to visualize on x-ray displays, contrast media may be either radiopaque or radiolucent. According to one exemplary embodiment, device 102 can include an exemplary one or more wire wrap or structural support 107, which can provide longitudinal and/or axial strength, which can be on a surface or embedded within sheath 104, according to an exemplary embodiment. According to an exemplary embodiment, the device 102 can further include, e.g., but not limited to, an exemplary one or more holes 108, which may be on the side 108, 109 of the plastic tube sheath 104, or on an end or tip 111, which may be used to infuse gas or fluid such as, e.g., but not limited to, an anti-coagulant such as, e.g., heparin, etc. according to an exemplary embodiment.

Example plastic tube sheath 104, according to an exemplary embodiment, can be manufactured from any of various other polymer materials, as will be apparent to those skilled in the relevant art, including, e.g., but not limited to, PS, ABS, SAN, PMMA, PPE, PP, PE, PA, PC, PET, PA, POM, PMP, PPP, PC-HT, PEI, PSU, PES, PPSU, PAI, PI, PVDF, ETFE, PCTFE, PTFE, ePTFE, PFA, LCP, PPS, PEEK, PEK, PEKEKK, FEP, PFA, nylons, fluoropolymers, LCP, engineered plastics, and/or etc. Example materials, which may be used to manufacture various embodiments disclosed herein may include, e.g., but not limited to, medical device materials available from any of various medical device vendors including Ensinger GmbH, Wilfried-Ensinger Strasse 1, 93413 Cham, Germany, according to an exemplary embodiment.

Exemplary inflator 112, according to one exemplary embodiment, can include one or more of a syringe, a hypodermic syringe, a pressurized cartridge, a pressurized gas cartridge, a compressor, a liquid and/or gas compressor, pneumatic and/or fluid, and/or $CO_2$ cartridge, etc. Thus, inflator 112 can include, in one embodiment a $CO_2$ cartridge, which can allow inflation of recessed balloon 116.

According to an exemplary therapeutic endovascular use, the balloon sheath catheter medical device 102 can be used to inflate via the exemplary inflator 112, the exemplary recessed integrated balloon sheath 116, with an inflated outer diameter 116A, having a recessed area that along occlusion balloon could blow up with $CO_2$ so it could be inflated and deflated rapidly, with a longer longitudinal axis balloon 116, inner diameter 116B, the recessed area allowing the balloon to be smaller when deflated, to allow withdrawal of exemplary balloon sheath medical device 130 and of sufficient diameter to remain in a constant position to occlude blood flow, during, e.g., implantation of an abdominal stent graft such as, e.g., but not limited to, a ANEURYX ENDURANT, or ENDURANT® II, stent grafts systems available from Medtronic Corporation of Minneapolis, Minn. USA and/or a GORE® EXCLUDER® AAA Endoprosthesis, available from Gore Medical, a division of W.L. Gore & Associates, Inc., Medical Products Division, Flagstaff, Ariz., USA.

Exemplary balloon sheath medical device 102 can further include an example one way valve 110, according to an exemplary embodiment, on a distal end of the device, according to an exemplary embodiment, to allow sheath medical device 102 to infuse fluid or gas such as e.g., but not limited to, anti-coagulant e.g., heparin, etc., and an elongated balloon 116 allowing device 102 to remain in a constant position to occlude blood flow, when the device is deployed in the upper thoracic region of the aorta, to ensure blood flow to the brain of a patient, during, e.g., implantation of an abdominal stent graft such as, e.g., but not limited to, an ENDURANT® II, stent grafts systems available from Medtronic Corporation of Minneapolis, Minn. USA and/or a GORE® EXCLUDER® AAA Endoprosthesis, available from Gore Medical, a division of W.L. Gore & Associates, Inc., Medical Products Division, Flagstaff, Ariz., USA.

Exemplary balloon sheath medical device 102 can further include an exemplary inflator 112, which can be coupled via one or more tubes, lumen, and/or multi-lumen tubing, valves, and/or ports, and/or couplers, 114, 120, 122 to an exemplary recessed balloon 116, according to an exemplary embodiment for ease of rapid inflation and/or deflation, according to an exemplary embodiment.

In one exemplary embodiment, the plastic tube conduit lumen 114, 115, 117 can run internal, integrated with, and/or external to plastic tube sheath 104. Exemplary plastic tube sheath 114 can be integrated into, internal to, external to, or adjacent to a side of plastic tube sheath 104, and can be used to inflate, using example inflator 112, example recessed balloon 116, which as depicted can be placed in a recess of tubular sheath 104, permitted eased extraction, particularly when withdrawing device 102 after graft implantation, according to an exemplary embodiment.

An exemplary recessed balloon 116, can in one embodiment be oblong in shape, oval, lengthened along one axis, tubular, or externally hot dog shaped and of longitudinal dimension of approximate 10-12 cm in length, and/or can allow for delivery over a wire, similar to a conventional spherical balloon catheter such as, e.g., but not limited to, the RELIANT balloon catheter, available from MEDTRONIC, of 710 Medtronic Parkway, Minneapolis, Minn. 55432 USA. The balloon material can be made of any exemplary medical grade material, such as, e.g., but not limited to, vinyl, nitrile, latex, silicone rubber, synthetic rubber, natural rubber, and/or vinyl latex, etc., according to an exemplary embodiment.

FIG. 1E depicts an exemplary embodiment of an exemplary external side view 140 of the exemplary balloon sheath medical device 102, also shown in FIG. 1A illustrating exemplary longitudinal axial strengthening wire wrapping 107, exemplary side holes 108, exemplary inflated recessed balloon catheter 116, according to an exemplary embodiment. As compared to FIG. 1A, FIG. 1E illustrated wire wrapping distal to side holes 108 and balloon 116 providing additional longitudinal strength as compared to wire wrapping merely proximal to side holes 108 of FIG. 1A.

Exemplary balloon sheath medical device 140 can include, in one example embodiment, exemplary wire 107 providing longitudinal axial strength, exemplary one or more holes 108, exemplary inflator 112, exemplary inflation tube 114, exemplary coupler 115, coupled internally or otherwise to exemplary inflated recessed balloon 116, according to an exemplary embodiment, which as depicted can be placed in a recess of tubular sheath 104.

FIG. 2 depicts an exemplary embodiment of an exemplary drawing 200 of an exemplary sheath medical device 202 illustrating exemplary longitudinal axial strengthening wire wrapping 107, with exemplary side holes 108 on a distal end, and with an exemplary flush tube 118, according to an exemplary embodiment. According to exemplary embodiments, the device of FIG. 3, or of FIG. 7 can be placed within the device illustrated in FIG. 2 and/or FIG. 5, according to exemplary embodiments.

Exemplary balloon sheath medical device 202 can include, in one example embodiment, exemplary wire 107 providing longitudinal axial strength, exemplary one or more holes 108, exemplary flush tube 118 can be used to infuse fluid, gas or otherwise coupled to exemplary sheath 104, according to an exemplary embodiment. The device 202 can be used along with a balloon occluder 702, such as that depicted and described, and as illustrated with respect to FIG. 7, below.

For further information with respect to FIG. 2, the reader is also directed to the description with reference to FIGS. 6A-6D, according to various exemplary embodiments.

Figure 3:
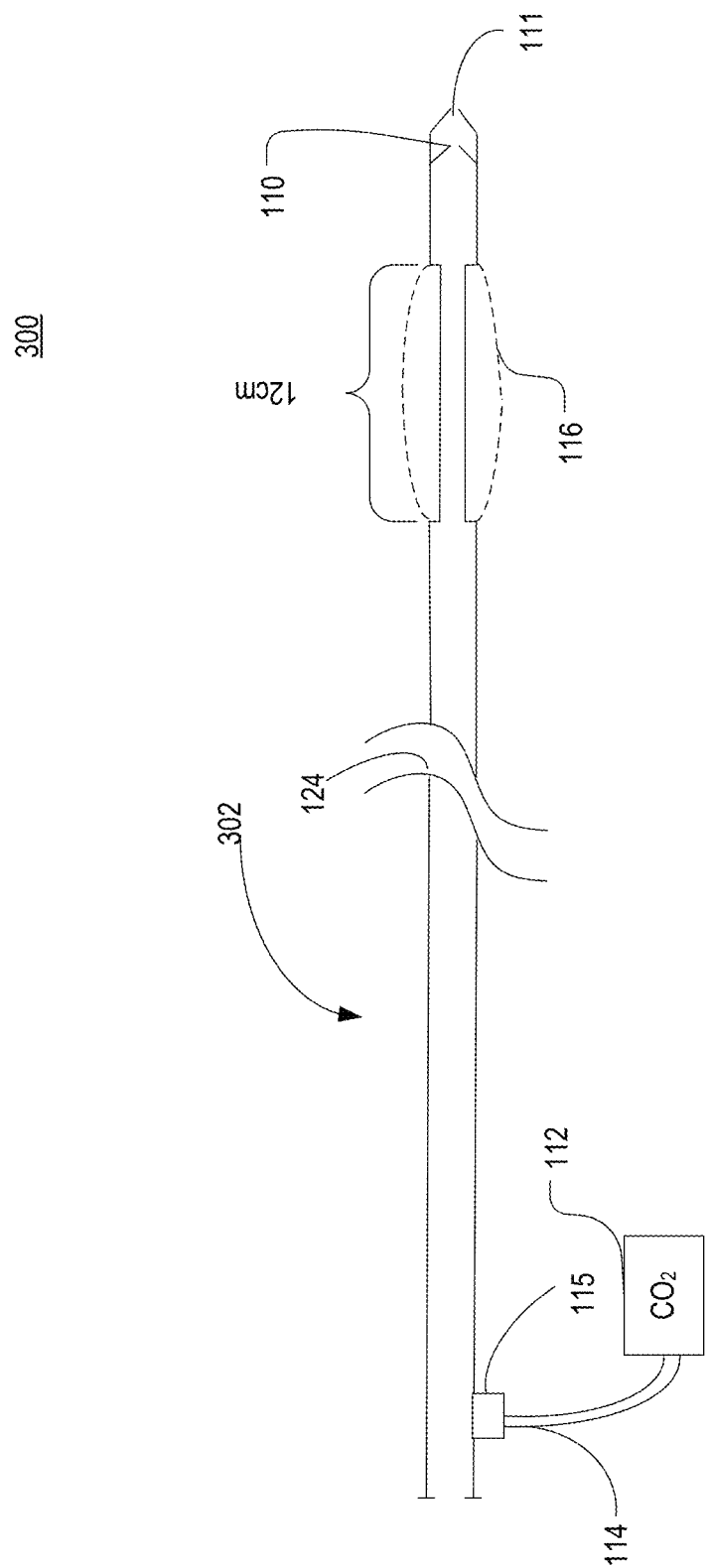
FIG. 3 depicts an exemplary embodiment of an exemplary drawing of an exemplary recessed integrated balloon sheath medical device with an exemplary valve, having an inflation device, such as, e.g., a $CO_2$ cartridge or other inflator, according to an exemplary embodiment.

FIG. 3 depicts an exemplary embodiment of an exemplary drawing 300 of an exemplary recessed integrated balloon sheath medical device 302 with an exemplary one way valve 110, at a distal tip 111 and having an exemplary inflation device 112, an exemplary recessed inflated balloon 116, exemplary atraumatic blunt or rounded tip 111, according to an exemplary embodiment. The balloon 116 can have a length of 8 cm -16 cm in one embodiment, and 10-12 cm preferably, according to an exemplary embodiment. According to an exemplary embodiment, the device illustrated in FIG. 3 can be made of an outer radius less than or close to substantially equal to an inner diameter of the device illustrated in FIG. 2, so as to allow the device of FIG. 3 to be used inserted within the device of FIG. 2, in an exemplary embodiment.

Exemplary balloon sheath medical device 302 can include, in one example embodiment, exemplary inflator 112, exemplary inflation tube 114, exemplary coupler 115, coupled internally to exemplary inflated balloon stint 116 with a length of about 10-12 cm, exemplary one way valve 110 on a right side distal end tip 111, exemplary atraumatic blunt tip 111, according to an exemplary embodiment.

Example plastic tube sheath 302 can be manufactured, according to an exemplary embodiment, from any of various other polymer materials, as will be apparent to those skilled in the relevant art, including, e.g., but not limited to, PS, ABS, SAN, PMMA, PPE, PP, PE, PA, PC, PET, PA, POM, PMP, PPP, PC-HT, PEI, PSU, PES, PPSU, PAI, PI, PVDF, ETFE, PCTFE, PTFE, ePTFE, PFA, LCP, PPS, PEEK, PEK, PEKEKK, FEP, PFA, nylons, fluoropolymers, LCP, engineered plastics, and/or etc. Example materials, according to an exemplary embodiment, which may be used to manufacture various embodiments disclosed herein may include, e.g., but not limited to, medical device materials available from any of various medical device vendors including Ensinger GmbH, Wilfried-Ensinger Strasse 1, 93413 Cham, Germany.

Exemplary inflator 112, according to one exemplary embodiment, can include one or more of a syringe, a hypodermic syringe, a pressurized cartridge, a pressurized gas cartridge, a compressor, a liquid and/or gas compressor, pneumatic and/or fluid, and/or $CO_2$ cartridge, etc. Thus, inflator 112 can include, in one embodiment a $CO_2$ cartridge, which can allow inflation of recessed balloon 116.

According to an exemplary therapeutic endovascular use, the balloon sheath catheter medical device 302 can be used to inflate via the inflator 112, the exemplary recessed integrated balloon sheath 116, having a recessed area that along occlusion balloon 116 could blow up with $CO_2$ so it could be inflated and deflated rapidly, e.g., but not limited to, an ENDURANT Stent graft, or ENDURANT® II, stent grafts systems available from Medtronic Corporation of Minneapolis, Minn. USA and/or a GORE® EXCLUDER® AAA Endoprosthesis, available from Gore Medical, a division of W.L. Gore & Associates, Inc., Medical Products Division, Flagstaff, Ariz., USA.

Exemplary balloon sheath medical device 302 can further include an example valve 110 on a distal end of the device, according to an exemplary embodiment, to allow sheath medical device 302 to remain in a constant position to occlude blood flow, when the device is deployed in the upper thoracic region 810 of the aorta, to ensure blood flow to the brain of a patient, during, e.g., implantation of an abdominal stent graft such as, e.g., but not limited to, an ENDURANT® II, stent grafts systems available from Medtronic Corporation of Minneapolis, Minn. USA and/or a GORE® EXCLUDER® AAA Endoprosthesis, available from Gore Medical, a division of W.L. Gore & Associates, Inc., Medical Products Division, Flagstaff, Ariz., USA.

For further information with respect to FIG. 3, the reader is also directed to the description with reference to FIGS. 6A-6D, according to various exemplary embodiments.

Exemplary balloon sheath medical device 302 can further include an exemplary inflator 112, which can be coupled via one or more tubes, lumen, and/or multi-lumen tubing, valves, and/or ports, and/or couplers 114, 115, to an exemplary recessed balloon 116, according to an exemplary embodiment.

An exemplary recessed balloon 116, can in one embodiment be oblong in shape, oval, lengthened along one axis, tubular, or hotdog like in external volume, and can be 10-12 cm and/or can allow for delivery over a wire 632, similar to a conventional spherical balloon catheter such as, e.g., but not limited to, the RELIANT balloon catheter, available from MEDTRONIC, of 710 Medtronic Parkway, Minneapolis, Minn. 55432 USA. The balloon material can be of any exemplary medical grade material, such as, e.g., but not limited to, vinyl, nitrile, latex, silicone rubber, synthetic rubber, natural rubber, and/or vinyl latex, etc.

Figure 4:
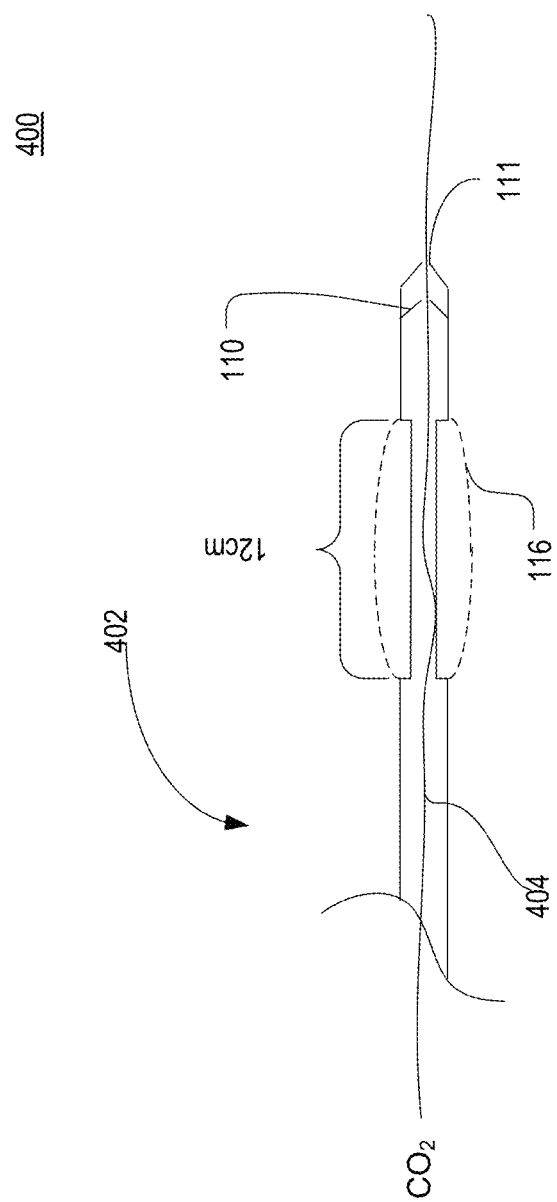
FIG. 4 depicts an exemplary embodiment of an exemplary drawing of an exemplary recessed integrated balloon sheath medical device having an exemplary one way valve on an exemplary tip, through which gas or other material may be infused, according to an exemplary embodiment.

FIG. 4 depicts an exemplary embodiment of an exemplary drawing 400 of an exemplary recessed integrated balloon sheath medical device 402 having an exemplary one way valve 110 on an exemplary tip 111, exemplary recessed inflated balloon stint 116, exemplary atraumatic blunt tip 111, according to an exemplary embodiment, through which gas 404 $CO_2$ or other material such as, e.g., but not limited to, anti-coagulants like heparin, etc. e.g., $CO_2$ may be infused, according to an exemplary embodiment.

Exemplary balloon sheath medical device 402 can include, in one example embodiment, a one-way valve 110 at the distal tip 111 to allow for, e.g., infusion, or introduction of radio-opaque (not permitting the passage of x-rays or other radiant energy) contrast medium that is injected into the body, introduced via catheter, to the upper thoracic region 810 of the aorta, to facilitate radiographic imaging of internal structures that otherwise are difficult to visualize on x-ray displays, contrast media may be either radiopaque or radiolucent, exemplary recessed inflated recessed balloon 116, exemplary atraumatic blunt tip 111 which may allow easier maneuvering of sheath throughout the artery.

Figure 5:
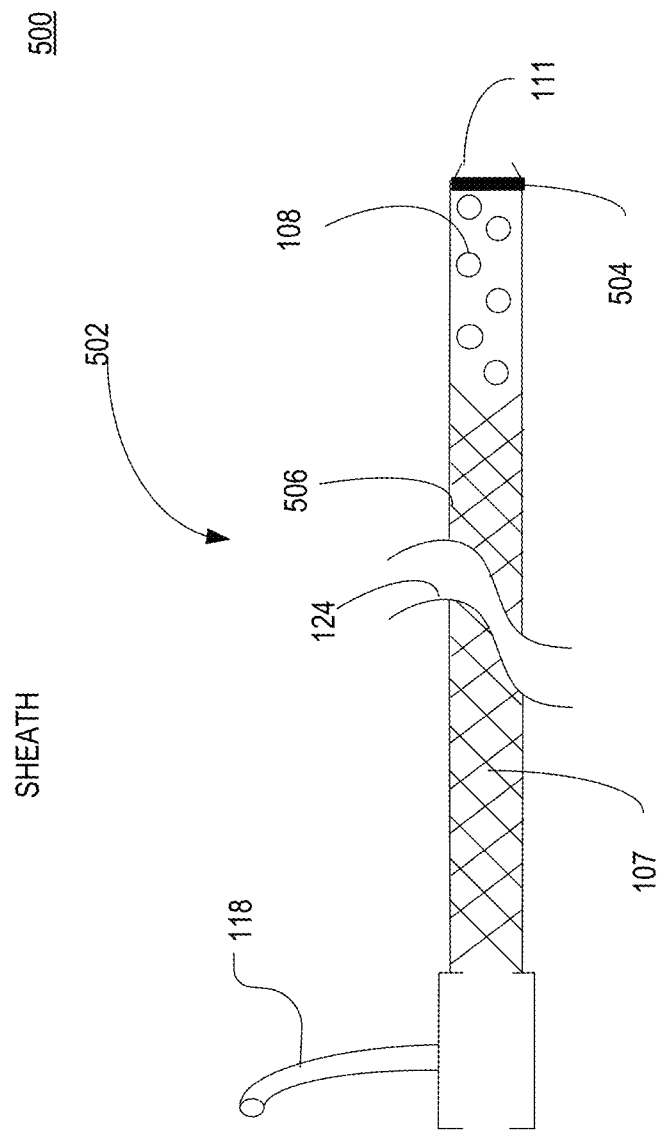
FIG. 5 depicts an exemplary embodiment of an exemplary drawing of an exemplary sheath medical device having an exemplary radio opaque tip and exemplary side holes, according to an exemplary embodiment.

FIG. 5 depicts an exemplary embodiment of an exemplary drawing 500 of an exemplary sheath medical device 502 having an exemplary axial longitudinal wire wrap (could even be parallel to the longitudinal axis) 107, exemplary sheath 506, exemplary side holes 108, exemplary atraumatic blunt tip 111, exemplary flush tube 118 coupled to sheath 506, exemplary radio opaque tip 504, according to an exemplary embodiment. According to exemplary embodiments, any other embodiments may include a radio opaque tip, according to an exemplary embodiment.

Exemplary balloon sheath medical device 502 can include, in one example embodiment, axial longitudinal wire wrap (could even be parallel to the long axis) 107, exemplary sheath 506, exemplary side holes 108, exemplary atraumatic blunt tip 111, exemplary flush tube 118 coupled to sheath 506, exemplary radio opaque tip 504, according to an exemplary embodiment.

Exemplary balloon sheath medical device 502 can be used to provide stiffness to an existing balloon occlude 702 (as discussed further below with reference to FIG. 7) for delivery over a wire 632, similar to a conventional spherical balloon occlude catheter 702, such as, e.g., but not limited to, the RELIANT balloon occluder catheter, available from MEDTRONIC, of 710 Medtronic Parkway, Minneapolis, Minn. 55432 USA.

Figure 6:
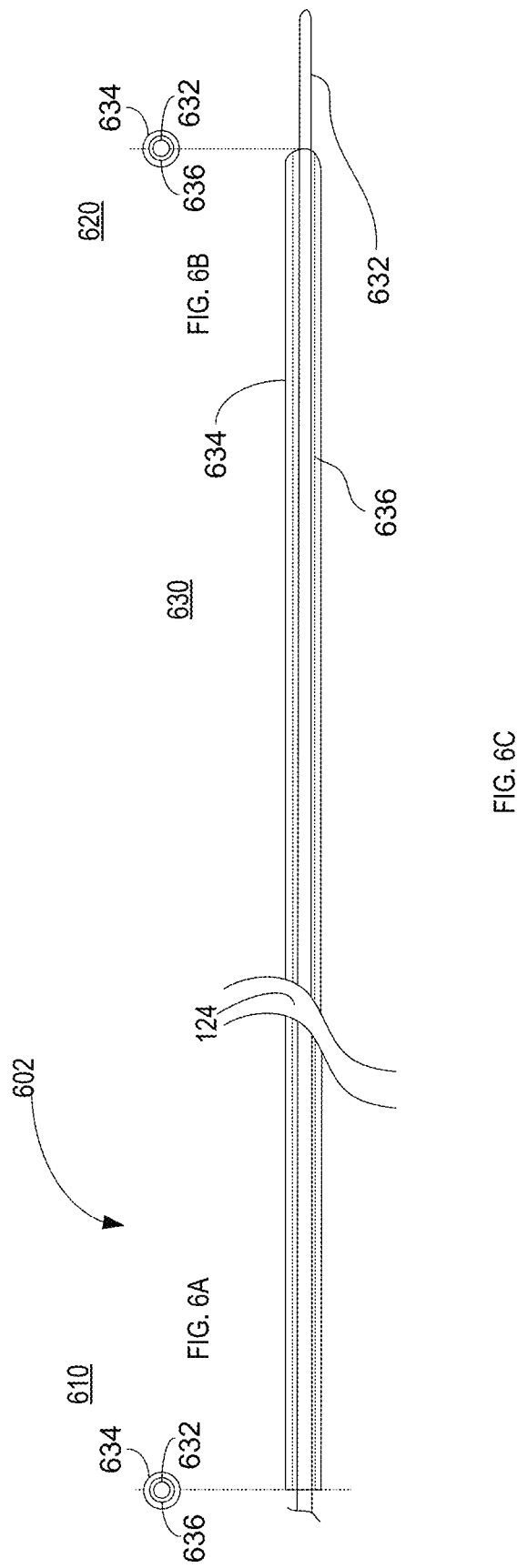
FIGS. 6A and 6B (collectively referred to FIG. 6) depict exemplary embodiments of exemplary drawings and, respectively, illustrating an exemplary left end view, and right end view, of an exemplary introducer, having an outer diameter, and a wire opening, according to an exemplary embodiment.
FIG. 6C depicts an exemplary embodiment of exemplary drawing, illustrating an exemplary side view of the exemplary introducer having an outer diameter, and a wire opening therethrough, with an exemplary atraumatic rounded tip for introducing the exemplary sheath medical device according to FIGS. 1-5, according to an exemplary embodiment.

FIGS. 6A and 6B (collectively referred to FIG. 6) depict exemplary embodiments of exemplary drawings 600 and 610, respectively, illustrating an exemplary left end view 610, and right end view 620, of an exemplary introducer 602, having an outer diameter 634, and a wire opening 636 or receiving wire 632, according to an exemplary embodiment. The reader is directed to the description with reference to FIG. 2, and FIG. 3 in reviewing the contents of FIGS. 6A-6D, according to various exemplary embodiments.

FIG. 6C depicts an exemplary embodiment of exemplary side view othegonal drawing 620, illustrating an exemplary side view 630 of the exemplary introducer 602 having an outer diameter 634, and a wire opening 636 therethrough, with an exemplary atraumatic rounded tip 111 for introducing the exemplary sheath medical device 102 according to FIGS. 1-5, according to an exemplary embodiment.

Figure 7:
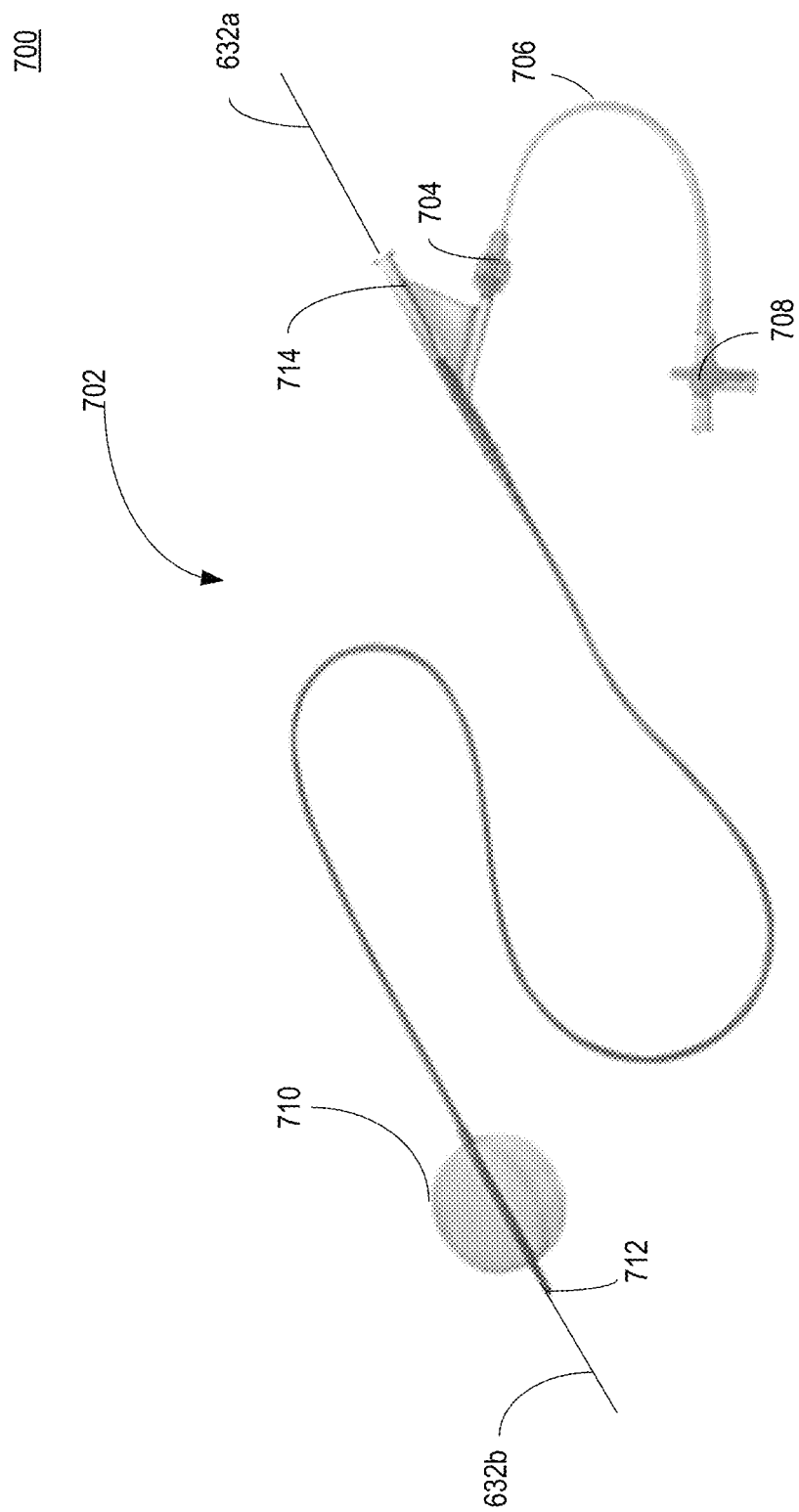
FIG. 7 depicts an exemplary embodiment of exemplary drawing, illustrating an exemplary over-the-wire, balloon catheter, as may be used in combination with various exemplary embodiments of the disclosure, according to an exemplary embodiment.

FIG. 7 depicts an exemplary embodiment of exemplary drawing 700, illustrating an exemplary over-the-wire, balloon occluder catheter 702, as may be used in combination with various exemplary embodiments of the disclosure, according to an exemplary embodiment, illustrating a conventional spherical balloon catheter such as, e.g., but not limited to, the RELIANT balloon catheter, available from MEDTRONIC, of 710 Medtronic Parkway, Minneapolis, Minn. 55432 USA, according to an exemplary embodiment. According to an exemplary embodiment, the balloon occluder catheter 702, may include balloon 710, and including a wire 632 via hole 712 at end 632b of the wire, and a hole 714 allowing end 632a of wire 632 to pass through the end 714, and infuser port 708, tube 706 and side port 704 of the balloon occlude catheter 702, according to an exemplary embodiment.

According to an exemplary embodiment, the balloon occlude catheter 702 can be used in combination with the device as depicted, in e.g., but not limited to, FIG. 2 and/or FIG. 5, according to exemplary embodiments.

FIG. 8 depicts an exemplary embodiment of exemplary drawing 800, illustrating an exemplary representation of a patient's peripheral arterial system, according to an exemplary embodiment. Exemplary embodiment of exemplary drawing 802, illustrating an exemplary representation of a patient's peripheral arterial system which, can include, among other arteries, exemplary common carotid arteries 802; exemplary subclavian artery 804; exemplary aortic arch 806; exemplary coronary artery 808; exemplary thoracic aorta 810; exemplary branches of the exemplary celiac trunk 814: exemplary left gastric artery 816, exemplary common hepatic artery 818, exemplary splenic artery 820; renal artery 822; radial artery 824; ulnar artery 826; common iliac 827; internal iliac artery 828; groin 830, and diaphragm 812 according to an exemplary embodiment.

General Background on AAA

When a patient has a ruptured aneurism and the patient is bleeding to death in the lower abdominal region a vascular surgeon will want to try and fix the aneurysm by installing an endograft stent, which involves entering from the patient's groin 830 (see FIG. 8) with a catheter, often delivered over a wire, and deploying, and fixing the graft stent remotely in the patient's abdomen, e.g., in the region of a ruptured aorta, e.g., in the area of the common iliac fork 827, according to an exemplary embodiment.

Sometimes what the surgeon must do, if performing abdominal surgery to treat a ruptured AAA, after opening the patient's belly up at the level of the diaphragm 812 the surgeon may put a clamp on the aorta 806, 810, according to an exemplary embodiment.

If the surgeon is going to be do this remotely, without opening the patient's abdomen, by, e.g., catheter through the groin, then the surgeon has to occlude the aortic artery, from inside the vascular system.

To treat a ruptured AAA, Applicant, an endovascular surgeon, in performing this procedure tried to place an endograft stent up from the groin 830 into the abdomen of the patient who is bleeding to death because the patient's aneurysm has ruptured. The vascular surgeon put a wire into the upper thoracic region of the aorta 810 and can insert a sheath over the wire, e.g., with a retractable introducer. Then a balloon occlusion catheter such as, e.g., but not limited to, that shown in FIG. 7 was attempted to be placed over the wire, and placed up into the upper thoracic aorta 810, above the level of the belly, i.e., above where the bleeding is occurring from the rupture, because the blood pressure in such a patient is very low from the internal bleeding. After occluding blood flow by inflating the balloon, the patient's blood pressure started to come up. Then, the conventional balloon catheter was found to bow caudally, getting pushed down with each heartbeat, and may became dislodged, preventing proper occlusion. So, to address this, the Applicant attempted overcoming this shortcoming of conventional balloon occluders by using a stiffer wire, but the same thing happened. Thus, to further address this, the Applicant surgeon attempted to put a bigger, larger flexible sheath up to support the balloon occluder, but still the same thing happened, i.e., the balloon migrated down from the bloodpressure. Meanwhile the patient was not doing well. So, finally the Applicant surgeon resorted to using a very large (approximately 28 Fr.) stiff sheath to attempt to support the balloon, which because of its large cross-sectional diameter would be hard to put up in most patients, but which in this particular patient, the Applicant did manage to get up. Then the Applicant vascular surgeon, who was supporting the balloon inflated the balloon up through the sheath and wedged the balloon in place with the stiff sheath so that the balloon occluder wound not fall.

After considering the shortcomings of his makeshift solution, the Applicant surgeon conceived of a better solution, as set forth herein. The solution, according to an exemplary embodiment, is to provide an improved occlusion device, which does not migrate when inflated. According to one embodiment the Applicant surgeon conceived of a medical device with a stiff sheath of less diameter than the larger stiff 28 Fr sheath previously used. In one exemplary embodiment, a small sheath such as that illustrated in FIG. 5, for example, with less diameter, e.g., 7-8 Fr, that is made of less thick than conventional rigid sheaths, but still of stiff plastic, stiffened by, e.g., but not limited to, a wire wrap on or embedded wiring in, the improved stiff sheath to provide rigidity, but with a smaller cross-section than conventional sheaths to allow for use in treatment of patients with, e.g., but not limited to, smaller vasculature, including that of, e.g., but not limited to, the elderly and patients of smaller stature or size. In one exemplary embodiment, a conventional balloon occluder catheter, such as, e.g., but not limited to, as shown in FIG. 7, can be supported by the improved stiffened sheath allowing use of the conventional occlude, and can provide additional features and advantages. In another exemplary embodiment, an improved balloon, of greater length along a length axis than conventional spherical balloon catheters, can be integrated in various exemplary embodiments, in an improved sheath, as disclosed herein.

In another embodiment, a sheath can be wire wrapped like that illustrated in FIG. 5, but can also include a balloon integrated together with the sheath, on or about the sheath, as opposed to these being two different things. The integrated sheath, having a smaller diameter than conventional stiff sheaths, which can be strengthened with, e.g., but not limited to, a wire mesh, etc., to give the sheath longitudinal support. Also, by elongating the balloon, as compared to conventional balloon occluders, say, e.g., but not limited to, 8-16 cm, 10-12 cm, or approximately 12 cm, were four times longer than conventionally, in an exemplary embodiment. The elongated balloon, has an advantage of having more surface area in contact with the wall of the vasculature, and can have greater surface contact to keep it in place, than the relatively small area of contact of a conventional balloon. A larger contact area in the thoracic aorta, according to an exemplary embodiment, can maintain the balloon occluder's and/or sheath's position, when longer in the longitudinal direction, for a length of approximately 10-12 cm, in one exemplary embodiment.

The example narrow stiff sheath, that is not as wide as conventional, but that has a wire wrap for longitudinal and/or axial stiffness, and an elongated balloon of approximately 12 cm exemplary length, and of which one can inflate an occluder balloon, can further include one or more side holes see FIG. 2 or FIG. 1A, 108, for example.

According to one exemplary embodiment, one can inject x ray dye to take pictures through hole(s) 108 or tip 111, see, e.g., but not limited to, FIG. 4. A one-way valve 110, 111, which in an embodiment can be at the distal tip of the sheath that when dye is injected can allow the dye to come out at a distal end, proximal to the balloon (at the side holes 108), or distal to the balloon, out the tip 111, in one embodiment.

Also, to help reduce the size of the sheath, according to one exemplary embodiment, a carbon dioxide inflation system 112, or other compressed gas, can be used to blow up/inflate the occluder balloon 116 as $CO_2$, as opposed to air or water, and an x-ray medium, which can require the diameter to be higher because the diameter necessary to get fluid up has to be greater because water is a fluid and is fairly viscous when there is x-ray dye mixed in it.

According to one embodiment Carbon Dioxide ($CO_2$) is a better solution, i.e., for inflation, because it shows up on an x-ray and may be used as an x-ray radio opaque medium when a patient has renal insufficiency, according to one exemplary embodiment.

An intra-aortic balloon pump, or angioballeen pump can be used to support a patient whose hemodynamics are bad, according to one exemplary embodiment. If a patient is really sick, a cardiologist can use a balloon pump and can use carbon dioxide to take a radio or x-ray picture because $CO_2$ enters and exits very quickly, according to one exemplary embodiment.

According to an exemplary embodiment, a roughly 7 to 8 Fr sheath can be provided as illustrated in FIG. 1, for example, and is shortened with example cutaway 124, to show example details of the exemplary working end. The end 111, according to an exemplary embodiment, can have an example one-way valve at the distal working end, i.e., distal to the balloon, and an embodiment of the sheath can have a recessed area that can house an exemplary elongated occlusion balloon 126, which can be inflated with $CO_2$, e.g., so it could be inflated rapidly and can be of a lower Fr cross-section, and can include optional hole(s) along the sides of the sheath, proximal to the balloon, and can have increased surface area contact with the vasculature side wall, due to its elongated balloon 126, and the exemplary recesses of one embodiment, can allow the balloon to be deflated and withdrawn, e.g., after implantation of a stent. Side holes, according to an exemplary embodiment, can allow an Angiogram or imaging or heparin or other anti-coagulant, or other type of infusion to be dispensed on a distal end, but proximal to the balloon, or via an example one way valve distal to the exemplary elongated balloon, according to an exemplary embodiment.

The exemplary side holes before the balloon, and example one way valve distal to the balloon, allow an angiogram to be performed distal to where the balloon occludes the bloodflow, or alternatively, the hole(s) and/or valve can be used to allow infusion of a heparin solution, or some type of anticoagulant, particularly, e.g., if used in trauma setting, according to an exemplary embodiment. The example longitudinal support wires, according to an exemplary embodiment, can, rather than being woven as illustrated, can in the alternative be wrapped circumferentially, and/or in a spiral like a spring, etc., according to an exemplary embodiment. The exemplary wiring can be in an axial orientation, or can provide longitudinal support for the sheath.

FIG. 2 illustrates an exemplary longitudinal support with exemplary wove wires wire wrap to give the exemplary sheath longitudinal support, to prevent bowing or bending of the sheath when blood pressure gets higher, so when there is forward pressure, when the blood pressure comes up, the exemplary sheath, according to an exemplary embodiment, does not bow due to the wire strengthener.

Exemplary Diameters for an Exemplary Sheath Medical Device

The exemplary sheath as illustrated in FIG. 1, can, in one exemplary embodiment be in the 7-9 french range. Preferably, the sheath should be as small as possible to both provide the longitudinal support necessary, as well as to allow endovascular insertion via the groin. According to one exemplary embodiment, the sheath can be 7-9 french (3 french=1 mm) so probably 3-4 mm in external diameter. Thus, this cross-sectional diameter is substantially smaller than most conventional sheaths of sufficient stiffness to support a balloon, without bowing. Various exemplary embodiments of the disclosed invention can be used in treating ruptured abdominal aneurysms and could also potentially have a role in providing balloon occlusion, in trauma patients, and resuscitative endovascular balloon occlusion of the aorta (REBOA), as well.

In a ruptured aneurysm, a vascular surgeon always positions the balloon occluder above the thoracic aorta. The idea is to stop blood flow to the lower extremities or the lower areas, to allow resuscitation to take place by anesthesia, to let fluids go in, to allow blood pressure to get back up, to allow blood pressure to be high enough to maintain blood flow to brain, which is the organ most susceptible to damage from the rupture. Thus, the occlusion arrests blood flow in the lower part of body so anything coming out of the heart will be pumped upwards, and maintains blood pressure to the brain, so brain injury is prevented.

In the case of resuscitative endovascular balloon occlusion of the aorta (REBOA) some endovascular balloon occlusion, is used in trauma situations. In the case of REBOA catheters, again conventional balloons are similar to the spherical balloon illustrated in FIG. 7, which do not have sufficient surface area to maintain position, and also lack a rigid sheath. According to an exemplary embodiment, a narrow rigid, non-bowing sheath can be provided and preferably with an integrated balloon, where the integrated balloon is an elongated balloon, of a minimum of 9 cm in length, in a range of approximately 10-16 cm, or more, in length, and preferably about 12 cm or more in length as illustrated in FIG. 3, and of a sufficient cross-sectional inflated diameter to fully occlude blood flow in the thoracic aorta, for example, of approximately 27-34 mm, about 30-40 mm, or up to 48 mm to provide for enhanced surface area contact, or up to 40-55 mm in diameter where the aorta is dilated or aneurysmic, according to an exemplary embodiment of the disclosure.

The one-way valve in various embodiments prevents blood from entering the sheath, according to an exemplary embodiment. The one-way valve is preferably at a distal end, beyond the balloon, so that when fluid is injected, the fluid can be ejected from the one-way valve distal to the balloon, as well as coming out the side holes before the balloon, as well, according to an exemplary embodiment. An exemplary lumen or tube can be used to inject fluid and/or the x-ray medium, according to an exemplary embodiment, and the fluid could come out of holes of the sheath behind the level of where the balloon is, according to an exemplary embodiment.

The balloon can be longer than conventional balloons, such as, e.g., but not limited to 12 cm in elongated form, surrounding the outside of the sheath, and can in certain embodiments, when deflated be recessed to ease when withdrawing the sheath after completion of the occlusion, and deflation of the balloon, according to an exemplary embodiment.

According to an exemplary embodiment, the balloon occlude can be inflated preferably with a separate and/or coupled, and/or connected by one or more tubes, ports, and/or valves, inflator, which can include, e.g., but not limited to, a gas inflator, such as, e.g., but not limited to, a $CO_2$ cartridge inflator 112, which could have one or more tube(s) 114, 120 122 running to allow the balloon 116 to inflate, as illustrated in FIGS. 1 and 3.

Because the balloon 116, according to an exemplary embodiment, is external one doesn't need to worry about interference of the sheath.

The wrapping wire, woven wire, and/or support wire and/or support structure preventing bowing of the sheath, in one exemplary embodiment, can end just below where the balloon is, just stopping at, or stopping somewhere close to, where the side hole(s) 108 can be placed as illustrated, e.g., in FIGS. 1A, 1E, 2 and/or 5, according to various exemplary embodiment.

The tubular sheaths, according to various exemplary embodiments can be made of some combination of plastic, some sort of polymer, any of various well known materials appropriate for surgical applications such as, e.g., but not limited to, a plastic and/or rubber and/or nylon and/or stiff plastic that is not prone to bending, but of sufficiently small cross section to be appropriate for endovascular insertion.

FIG. 6 sets forth an exemplary introducer, the thing that allows one to pass a device over a wire, (the introducer has a small diameter hole through its center allowing the introducer to be guided over a small diameter wire). The introduce allows a medical device to be delivered endovascularly over a wire and not have the medical device be blunt. An introducer would be used to provide the medical device over the wire. After insertion of the device, the introducer can be withdrawn leaving the medical device positioned where desired, such as, e.g., in the thoracic aorta. The introducer would have a rounded, non-atraumatic point, one that is less pointed, more blunt.

The introducer sheath could have something that could go through the middle of the sheath, that is safe so as not to damage the sheath, or one way valve at the distal end of the sheath, there could be a mark on a proximal end to indicate where the introducer should not be pushed any further forth so that the surgeon inserting the medical device can know that the tip of the introduce can extend out only partially through the tip of the sheath, just barely out through the one way valve so that the device can be provided over a wire using the introducer, according to an exemplary embodiment.

An adjunct, according to an exemplary embodiment, can be to try to maintain hemodynamics in a patient whose hemodynamics are deteriorating, or unstable. Primarily when caused by a ruptured aneurysm, but also the case of a trauma patient (e.g., in the REBOA application).

In the case of trauma patients there is about a 10% chance of blot clots forming down in the lower part of the body after they use a balloon occlude catheter. Although a trauma patient may be being treated, a physician can provide a low dose of blood thinner administered intra-arterially to mitigate some of the risk of blood clots forming in the lower abdomen from the use of the balloon occluder, according to an exemplary embodiment. The 10% incidence is significant and the side holes and/or one way valve can provide an option to allow infusion of e.g., anti-coagulants, and/or other injection such as, e.g., but not limited to, a saline infusion, or to keep a little flow distal to where they are using the occlusion balloon.

When treating a ruptured aneurysm, a surgeon can administer an anti-coagulant such as, e.g., but not limited to, heparin, which can be circulated throughout the body. One might not do this if the application were in a trauma setting, but there can be some situations as noted, where a low dose may be useful, according to an exemplary embodiment.

The balloon, according to an exemplary embodiment, could be a little recessed such as in a cavity as shown in FIG. 1A (in the sheath 104) along the side so when the balloon 116 is deflated after no longer needed, the whole medical device 102 can be pulled back down the (out) side the endograft that has been already deployed. So, you might have a situation where the endograft was up, and the balloon has been inserted going e up alongside external but adjacent to the endograft stent, and after deploying the graft the surgeon wants to be able to pull the medical device 102 back down and get it back out. So, by recessing the balloon in a slight cavity in the sheath, in an area 126, which is a little bit recessed, so that the balloon when deflated is relatively flush with the outer diameter 106 of the sheath medical device 102, according to an exemplary embodiment. Thus, the device 102 can be pulled back and because the balloon 116 is recessed when deflated, the balloon does not catch on the graft when retracted alongside the stent.

Summary

Thus, the idea was conceived when Applicant was treating a patient with a ruptured aneurysm, the patient's blood pressure was really low, while delivering standard RELIANT vascular aortic balloon occluder. As the patient's blood pressure came up, the catheter was bowing back upon itself and pushing back down into the aneurysm itself. The treatment required multiple manipulations, and ultimately it required delivery of a pretty large sheath approximately 24 Fr, to buttress a balloon occluder at the back of the balloon with the large diameter sheath. Conventionally Applicant was able to amalgam several systems to attempt to accomplish this, but only by combining together a very large, stiff sheath (less than optimal) and a conventional spherical balloon occluder, but certainly nothing is available as set forth in the various exemplary embodiments set forth in this disclosure; i.e., nothing is available, which is as clean, nor integrated, nor as low profile as set forth herein. Also, conventionally one has to go up fairly high on a sheath size to get something delivered that can actually support a balloon, and that is a problem if a patient has small arteries. Typically, a small or lower profile system that accomplishes the same result is better than something that is larger. In an exemplary embodiment, an improved sheath of 6-7 Fr diameter can be provided with wire support to provide longitudinal strength. In one embodiment, the balloon can be 12 cm long, as opposed to 2 cm-3 cm for the RELIANT balloon shown in FIG. 7. With an elongated balloon, there is a lot more cohabitation against the wall of the aorta or the vessels where the occlusion is taking place.

The balloon according to an exemplary embodiment would be an elongated, oval balloon with an elongated dimension of 10-16 cm, and therefore increased surface are in contact with the vascular wall. The balloon could otherwise be somewhat like the RELIANT Balloon Occluder 702, available from Medtronic of Minneapolis, Minn. USA, i.e., there would be a hole 712 down the end of the tip of the balloon 710 occluder, however the balloon of the disclosure would be an elongated, hot dog shaped balloon (not shown in FIG. 7), according to an exemplary embodiment. A wire 632b that can go through the holes 712, 714 and there can be separate side ports and/or valves and/or lumen 704, 706, 708 that can be used to inflate the balloon.

RELIANT Balloon 710 as illustrated, includes to the side an inflation port and there is a little connection between inflation port and where the balloon blows up, as opposed to this one. Applicant's balloon occluder 102 can also include such a side port, which can be for inflation, or another side port can allow infusion, etc.

Further, a wire would go through device and serve to guide the device to its desired location to allow occluding bloodflow in the aorta, by inflating the elongated balloon as set forth in Applicant's claimed invention. The wire 632 serves as a guide; the wire guides delivery of the medical device intravascularly to the general vicinity for deployment.

Balloon occlusion can have a goal of stopping blood flow to the lower extremities, to allow resuscitation to take place by, e.g., anesthestia, etc., allowing maintaining of blood flow to the brain. A role for a balloon occlusion in Trauma REBOA aspects, a low dose blood thinner may be administered intra-arterially, or at least as a saline infusion, to keep a flow distal to the occlusion.

As noted, the balloon would be recessed when deflated along the side of the sheath in a recess in the sheath, so that the sheath can be then withdrawn from the endograft. The balloon and sheath are alongside the graft, and then when pulled back do not catch.

In the case of a ruptured aneurysm, low blood pressure, an elongated balloon can be placed and supported by a stiff sheath, preferably of smaller cross-section but strengthened to support the exemplary elongated balloon, which can then allow the patient's blood pressure to come back up, while the stiff sheath can prevent the elongated balloon occluder from bowing and losing occlusion. The exemplary sheath can buttress the back of, or be integrated with the balloon so as to prevent caudal movement of the balloon, and to ease expeditious implant of a graft stent.

All examples and conditional language recited herein are intended for pedagogical purposes to aid the reader in understanding the principles of the disclosure and the concepts contributed by the inventor to furthering the art, and are to be construed as being without limitation to such specifically recited examples and conditions. Moreover, all statements herein reciting principles, aspects, and embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. A medical device comprising:
  a stiffened sheath comprising:
    a narrow cross-section, wherein said narrow cross-section comprises:

an external cross-sectional outer diameter of at least one or more of:
5-10 Fr (1.667 mm-3.333 mm);
7-8 Fr;
7-9 Fr;
8 Fr;
greater than 5 Fr but less than 14 Fr;
24 Fr; or
greater than 5 Fr but less than 28 Fr; and
for use intraluminally in the vasculature of a patient; and
an elongated balloon occluder disposed at a working distal end of said stiffened sheath,
wherein said elongated balloon occluder comprises:
an elongated balloon comprising:
a longitudinal length along a longitudinal axis of greater than an inflation diameter of said elongated balloon,
wherein the longitudinal length of said elongated balloon comprises at least one or more of:
8 cm-16 cm;
10 cm-12 cm;
10 cm-16 cm;
between 9-15 cm (270-450Fr, or 90 mm-150 mm);
8 cm;
9 cm;
10 cm;
11 cm;
12 cm (360Fr, or 120 mm);
13 cm;
14 cm;
15 cm; or
16 cm.

2. The medical device according to claim 1, wherein said sheath comprises:
woven wire reinforcing axial and longitudinal strength.

3. The medical device according to claim 2, wherein said woven wire comprises:
wherein said woven wire forms a mesh circumferentially embedded or adjacent to a lumen of said sheath.

4. The medical device according to claim 1, wherein said narrow cross-section sheath comprises an external cross-sectional diameter of at least one or more of:
6-9 Fr (2 mm-3 mm);
6-7 Fr (2 mm-2.333 mm); or
5-8 Fr (1.667 mm-2.667 mm).

5. The medical device according to claim 1, wherein said sheath comprises:
at least one hole.

6. The medical device according to claim 5, wherein said at least one hole of said sheath comprises at least one or more of:
at least one side hole;
a one-way valve;
a one-way valve at a distal tip of said sheath; or
a one-way valve on a distal end, distal to said balloon.

7. The medical device according to claim 6, wherein said sheath further comprises:
a lumen comprising at least one channel for use in dispensing via said at least one hole at least one or more of:
a radio opaque dye;
a radio opaque gas;
an x-ray radio opaque medium;
a $CO_2$ gas;
a compressed gas;
a gas when coupled to an inflator;
a compressed gas when coupled to a canister or cartridge;
$CO_2$ gas from a $CO_2$ cartridge coupled to said lumen;
$CO_2$ gas from a $CO_2$ canister coupled to said lumen;
a gas when coupled to a balloon pump;
a gas when coupled to an intra-aortic balloon pump;
a gas when coupled to an angioballeen pump;
a gas when coupled to a gas inflation cartridge;
a gas when coupled to a gas inflation canister;
a gas when coupled to a gas inflation pump;
a gas or liquid when coupled to a syringe;
an anti-coagulant;
a heparin injection;
a heparin infusion; or
a drug.

8. The medical device according to claim 5, wherein said at least one hole of said sheath comprises:
a plurality of side holes; and
a one-way valve on a distal end, distal to said balloon.

9. The medical device according to claim 1, wherein said sheath further comprises:
a lumen comprising at least one internal channel for use in dispensing at least one or more of:
a radio opaque dye;
anti-coagulant; or
a drug.

10. The medical device according to claim 1, wherein said elongated balloon comprises:
wherein said elongated balloon is recessed in a cavity in said sheath.

11. The medical device according to claim 1, wherein said elongated balloon comprises: wherein said elongated balloon is integrated coaxially in a cavity in said sheath.

12. The medical device according to claim 1, wherein said elongated balloon is inflatable and comprises:
wherein said elongated balloon is coupled to an inflator.

13. The medical device according to claim 12, wherein said elongated balloon and said inflator are coupled together via at least one or more of:
a lumen; or
an inflation port.

14. The medical device according to claim 12, wherein said inflator comprises at least one or more of:
a syringe;
a compressed gas source;
a fluid source;
a $CO_2$ cartridge;
a hypodermic syringe;
a pressurized air;
a pressurized gas; or
a pressurized liquid.

15. The medical device according to claim 1, wherein said elongated balloon comprises at least one or more of:
an oval shape;
is inflatable; or
wherein said elongated balloon comprises the inflation diameter of at least one or more of:
10 mm-60 mm (30-150Fr);
15 mm-48 mm (45-144Fr);
10 mm-48 mm;
15 mm-60 mm;
15 mm-44 mm;
44 mm-48 mm;
44 mm-60 mm;
48 mm-60 mm; or
44 mm (132Fr).

16. The medical device according to claim 1, wherein said elongated balloon comprises:
wherein said elongated balloon has the longitudinal length of at least one or more of:
greater than or equal to (270Fr, or 90 mm); or
greater than or equal to 12 cm (360Fr, or 120 mm).

17. The medical device according to claim 1, further comprising:
a lumen coupled to said sheath wherein said lumen is configured to:
flush said sheath; or
inject gas or fluid through said sheath.

18. The medical device according to claim 1, further comprising at least one or more of:
a wire for passing the medical device through the vasculature of a patient;
an introducer;
an atraumatically tipped introducer;
a rounded end introducer;
an introducer configured to introduce the medical device through the vasculature of a patient; or
an introducer configured to pass over a wire the medical device.

19. The medical device according to claim 1, wherein said sheath comprises at least one polymer material comprising at least one or more of:
PS, ABS, SAN, PMMA, PPE, PP, PE, PA, PC, PET, PETE, PETP, PET-P, Bio-PET, PA, POM, PMP, PPP, PC-HT, PEI, PSU, PES, PPSU, PAI, PI, PVDF, ETFE, PCTFE, PTFE, expanded PTFE, ePTFE, PFA, LCP, PPS, PEEK, PEK, PEKEKK, FEP, PFA, nylon, fluoropolymer, LCP, a suitable synthetic material, or engineered plastic;
wherein said engineered plastic comprises at least one or more of:
polyvinyl chloride (PVC),
polypropylene,
Polyethylene, or
Polystyrene.

20. The medical device according to claim 1, wherein said stiffened sheath comprises at least one or more of:
a metal wire;
a metal wire reinforcement;
a longitudinal metal wire;
wire mesh;
wire material mesh;
a shape memory wire;
a shape memory metal;
a Nitinol material;
a steel material;
a medical wire;
longitudinal strength reinforcement;
longitudinal strengthening material;
wire longitudinal strength reinforcer;
woven strengthener;
woven material;
wire reinforcement;
metal reinforcement;
mesh material;
support wire;
supporting material;
wrapping material;
woven wire;
strengthening wrap;
medical grade material;
metal material; or
metal longitudinal strengthener.

21. The medical device according to claim 1, wherein said combination of said stiffened sheath with said elongated balloon provides an increase in length of vascular wall apposition, and results in increased resistance to movement of the medical device, and decreases or eliminates balloon migration during treatment of trauma or abdominal aortic aneurysm (AAA).

22. The medical device according to claim 1, wherein said stiffened sheath and said elongated balloon are configured to be delivered over a wire.

23. A medical device comprising:
a stiffened sheath comprising:
a narrow cross-section,
wherein said narrow cross-section comprises:
an external cross-sectional outer diameter of at least one or more of:
5-10 Fr (1.667 mm-3.333 mm);
7-8 Fr;
7-9 Fr;
8 Fr;
greater than 5 Fr but less than 14 Fr;
24 Fr; or
greater than 5 Fr but less than 28 Fr; and
for use intraluminally in the vasculature of a patient; and
wherein said stiffened sheath comprises:
longitudinal strength reinforcement; and
an elongated balloon occluder disposed at a working distal end of said stiffened sheath,
wherein said elongated balloon occluder comprises:
an elongated balloon comprising:
wherein said elongated balloon comprises:
a longitudinal length of at least one or more of:
8 cm-16 cm;
between 9-15 cm;
10 cm-12 cm;
10 cm-16 cm;
8 cm;
9 cm;
10 cm;
11 cm;
12 cm;
13 cm;
14 cm;
15 cm; or
16 cm.

24. A method of making a medical device comprising:
extruding a tubular strengthened stiffened sheath lumen;
wherein said stiffened sheath lumen comprises:
a narrow cross-section,
wherein said narrow cross-section comprises:
an external cross-sectional outer diameter of at least one or more of:
5-10 Fr (1.667 mm-3.333 mm);
7-8 Fr;
7-9 Fr;
8 Fr;
greater than 5 Fr but less than 14 Fr;
24 Fr; or
greater than 5 Fr but less than 28 Fr; and
coupling an elongated balloon at a distal end of said stiffened sheath lumen,
wherein said elongated balloon comprises:
a longitudinal length of at least one or more of:
8 cm-16 cm;
between 9-15 cm;
10 cm-12 cm;

10 cm-16 cm;
8 cm;
9 cm;
10 cm;
11 cm;
12 cm;
13 cm;
14 cm;
15 cm; or
16 cm.

* * * * *